US012369967B2

(12) United States Patent
Travers et al.

(10) Patent No.: US 12,369,967 B2
(45) Date of Patent: Jul. 29, 2025

(54) APPARATUS AND METHOD FOR OPTIMIZING AND ADAPTING TREATMENT OF MULTIPLE TUMORS IN PATIENTS WITH METASTATIC DISEASE BY ELECTRIC FIELD

(71) Applicant: LifeBridge Innovations, PBC, Longwood, FL (US)

(72) Inventors: Peter F. Travers, Longwood, FL (US); Richard Rotondo, Oviedo, FL (US); Scott Krywick, Lake Mary, FL (US); Nathaniel R. Travers, Longwood, FL (US); Ken Watkins, Lake Mary, FL (US)

(73) Assignee: LifeBridge Innovations, PBC, Longwood, FL (US)

( * ) Notice: Subject to any disclaimer, the term of this patent is extended or adjusted under 35 U.S.C. 154(b) by 877 days.

(21) Appl. No.: 17/111,204

(22) Filed: Dec. 3, 2020

(65) Prior Publication Data

US 2021/0177492 A1     Jun. 17, 2021

Related U.S. Application Data

(60) Provisional application No. 62/948,600, filed on Dec. 16, 2019.

(51) Int. Cl.
| | | |
|---|---|---|
| *A61N 1/32* | (2006.01) | |
| *A61B 18/14* | (2006.01) | |

(Continued)

(52) U.S. Cl.
CPC ............... *A61B 18/14* (2013.01); *A61N 1/32* (2013.01); *A61B 2018/00077* (2013.01);

(Continued)

(58) Field of Classification Search
CPC .......... A61B 18/14; A61B 2018/00077; A61B 2018/00083; A61B 2018/0016; A61B 2018/00791; A61B 2018/1467; A61N 1/32

(Continued)

(56) References Cited

U.S. PATENT DOCUMENTS

| | | | | |
|---|---|---|---|---|
| 6,868,289 | B2 * | 3/2005 | Palti .................. | A61N 1/40 607/76 |
| 8,706,261 | B2 * | 4/2014 | Palti .................. | A61N 1/40 607/2 |

(Continued)

FOREIGN PATENT DOCUMENTS

| | | | | |
|---|---|---|---|---|
| WO | WO-2011130495 A1 * | 10/2011 | ............... | C12Q 1/68 |
| WO | WO-2015138385 A1 * | 9/2015 | ........... | A61B 5/0263 |

*Primary Examiner* — Carl H Layno
*Assistant Examiner* — Anh-Khoa N Dinh
(74) *Attorney, Agent, or Firm* — TAYLOR & EDELSTEIN, PC

(57) ABSTRACT

A method of delivering tumor treating electric fields to a body of a patient. The method includes scanning the body of the patient for identifying at least two tumor-filled areas. The method further includes determining a spatial relationship in between the at least two tumor-filled areas. The method further includes arranging an array of insulated electrode elements on the body of the patient. The method further includes implementing at least two subarray firing configurations for the array of insulated electrode elements to treat the at least two tumor-filled areas depending at least in part upon the spatial relationship in between the at least two tumor-filled areas such that each subarray firing configuration treats a respective tumor-filled area.

24 Claims, 16 Drawing Sheets

(51) Int. Cl.
 *A61N 1/04* (2006.01)
 *A61N 1/36* (2006.01)
 *A61N 1/40* (2006.01)
 *A61B 18/00* (2006.01)

(52) U.S. Cl.
 CPC .............. *A61B 2018/00083* (2013.01); *A61B 2018/0016* (2013.01); *A61B 2018/00791* (2013.01); *A61B 2018/1467* (2013.01)

(58) Field of Classification Search
 USPC ............................................................ 607/2
 See application file for complete search history.

(56) References Cited

U.S. PATENT DOCUMENTS

| | | | |
|---|---|---|---|
| 9,370,304 B2* | 6/2016 | Cao ...................... | G06T 7/0016 |
| 2005/0203578 A1* | 9/2005 | Weiner .................... | A61N 5/00 |
| | | | 607/2 |
| 2006/0276858 A1* | 12/2006 | Palti .................... | A61N 1/0408 |
| | | | 607/76 |
| 2009/0187183 A1* | 7/2009 | Epstein .............. | A61B 18/1233 |
| | | | 606/41 |
| 2016/0000504 A1* | 1/2016 | Manning ................. | A61N 5/00 |
| | | | 607/100 |

* cited by examiner

APPARATUS AND METHOD FOR OPTIMIZING AND ADAPTING TREATMENT OF MULTIPLE TUMORS IN PATIENTS WITH METASTATIC DISEASE BY ELECTRIC FIELD

CROSS REFERENCE TO RELATED APPLICATIONS

This is a non-provisional application based upon U.S. provisional patent application Ser. No. 62/948,600, entitled "APPARATUS AND METHOD FOR OPTIMIZING AND ADAPTING TREATMENT OF MULTIPLE TUMORS IN PATIENTS WITH METASTATIC DISEASE BY ELECTRIC FIELD", filed Dec. 16, 2019, which is incorporated herein by reference.

BACKGROUND OF THE INVENTION

1. Field of the Invention

The present invention relates to the selective destruction of multiple solid tumors in large areas encompassing the entire torso of metastatic cancer patients. More particularly, the present invention relates to an apparatus and method for optimizing the destruction of multiple tumors while not damaging normal cells, and further adapting the optimization of the destruction of multiple tumors over time as changes in size, a number of, and location of multiple tumors occur within a metastatic patient.

2. Description of the Related Art

Alternating Electric Fields, also referred to as Tumor Treating Fields (TTF's), can be employed as a type of cancer treatment therapy by using low-intensity electromagnetic fields. These low-intensity fields rapidly change direction, thousands of times per second. Since the TTF's are electric fields, they do not cause muscle twitching or severe adverse side effects on other electrically activated tissues. The growth rate of metastatic diseases is typically greater than the growth rate of normal, healthy cells. Alternating Electric Fields therapy takes advantage of this high growth-rate characteristic. TTF's act to disrupt a cancer cell's mitotic process and cytokinesis by manipulating the cell's polarizable intracellular constituents, namely tubulins that form mitotic spindles that pull the genetic material in the nucleus into two sister cells. TTF's interrupt mitotic spindle microtubule assembly thereby preventing cell division. The metastatic disease cells treated using TTF's will go into programmed cell death usually within 4 to 5 hours. The result is a significant reduction in tumor size and potential for full elimination of solid tumors. TTF's are tuned to treat specific cancer cells and thereby do not damage normal cells. TTF therapy can be used as a sole treatment method, or it can be combined with conventional drug delivery mechanisms.

The following is an explanation of how electric fields selectively kill cancer cells. The basic physics of using electric fields to trigger an immunogenic response to selectively kill cancer cells involves commonly known attributes of charged particles. That is, like charges repel and opposite charges attract. Key protein(s) essential to mitosis have high dipole moments. That is, they are negative on one side and positive on the other.

In a constant field charged particles will migrate towards opposite charges. Under exposure to an alternating electric field, dipole proteins essential to mitosis rotate back and forth with the alternating charge of the field.

Electric fields that lead to cancer cell death are those created through solid tumors at frequencies between 100 hKz and 300 hKz, depending on the size of the cancer cells. The question to answer first is what within the cancer cell is the electric field interactive with to disrupt tumor growth.

A key protein complex involved in mitosis is Septin, which has a very high dipole moment. Septins have many functions and are involved in cell structural support. In the presence of an alternating electric field, at the optimal frequency, the localization of Septin needed to carry out its functions is diminished. The result of electric field exposure during mitosis does not prevent tumor daughter cells from being formed but does cause them to be malformed. The foreign nature of daughter cells developed under the optimal electric field is such that an immune response is triggered. Immunogenic cell death occurs, resulting in diminished tumors.

The above mechanism of action using Septin can be further validated by the fact that patients under electric field therapy for glioblastoma who have compromised immune systems (CD8 cell count<144 cells/mm$^2$, CD4/CD8 ratio<1.09) do not respond to electric field therapy as compared to those with healthy immune systems. Such patients with compromised immune states may receive no benefit from receiving therapy.

Of course, the results of therapy may depend on a properly tuned electric field which may penetrate the cell wall. Whether an electric field can penetrate a cancer cell wall is dependent on the relationship of the frequency of the field to the size of a cell.

There is an inverse relationship between the effective electric field frequency and the size of the cancer cell. The larger the cancer cell the lower the frequency needed to penetrate its cell wall. The smaller the cancer cell the higher the frequency needed to push through the cell wall. In fact, the efficacy of electric fields in reducing solid tumors is frequency dependent and each cancer cell type can have a specific frequency for which the inhibitory effect is greatest. Thereby, the selection of which metastatic cancers to treat with adaptive electric field therapy may be determined in part by cell size range. There is no other attribute that indicates electric fields should be used on one cancer over another because its mechanism of action is based on disturbing the most universal process of all cancer cells, mitosis. As long as the cancer chosen for treatment can be effectively treated within the frequency ranges shown to not harm normal cells 100 kHz-300 kHz.

A secondary mechanism of action of sending select electric fields through solid tumors is called Dielectrophoresis. Electric fields may push polarizable macromolecules and/or organelles toward the mitotic furrow during late stage mitosis. This often causes the cleavage furrow to burst, causing cell destruction. This secondary killing action is achieved when the line of the electric field is parallel to the line of the cleavage furrow. When the electric field and the line of the cleavage furrow are perpendicular, dielectrophoreses does not take place. Because the axis of division (the line of the cleavage furrow) may be random in cancer tumors, it may be that only a fraction of cells is getting exposure to possible dielectrophoresis when only one angle field is delivered. It may be impossible to achieve enough angles to create this phenomenon at the level required to eliminate a tumor. Nonetheless, increased tumor reduction can be achieved by adding additional angles to therapy.

In addition to frequency, and the number of angles of delivery (dielectrophoresis) there are other variables that may influence the success of electric field therapy to reduce tumors. Among them are the intensity of the field, the speed of switching from one angle to the next, and patient compliance.

Known devices and methodology for treating tumors focuses on localized tumors. Hence, prior art treatments with dedicated array elements may not have enough versatility to adequately address multiple disease locations.

What is needed in the art is a device and method that takes a more comprehensive and adaptive approach to treating late stage widespread cancer over time.

SUMMARY OF THE INVENTION

The present invention relates to an apparatus and method for optimizing the destruction of multiple solid tumors and/or diffuse tumors throughout the human torso, by maximizing the benefit of the immunogenetic response caused by specifically tuned electric fields.

The present invention provides a solution, which optimizes an immunogenic response to reduce multiple/diffuse solid tumors. Thereby, the present invention focuses on diffuse disease or disease in multiple locations in patients with advanced cancer. The present device accomplishes this through:

1. Treating multiple TTFields (two or more strategic areas treated simultaneously and/or in rotation).
2. Adapting the delivering of multiple or simultaneous electric fields by the spatial relationship of multiple tumors to each other and vital organs.
3. Tracking and changing the intensity of the electric fields as it changes in response to changes in other variable (angles, frequency, interaction with other fields, etc.). In order to optimize the effectiveness of the intensity of the electric field.
4. Maximum number of delivery angles (to reduce duty cycles of array elements).
5. Frequency of the tumor treating field and adapting all other variables when a change in frequency is made.
6. Adapting therapy to patient compliance.
7. Using predictive data, such as predictive blood work and/or predictive modeling, to design a preventive therapy regimen to minimize the likelihood of reoccurrence once remission has been achieved.

The apparatus and method of the present invention allow for each of these variables to be applied more effectively, thereby making electric field therapy to treat solid tumors available to metastatic cancer patients with diffuse disease or disease in two or more locations.

The present invention in another form is directed to a method of delivering tumor treating electric fields to a body of a patient. The method includes scanning the body of the patient for identifying at least two tumor-filled areas. The method further includes determining a spatial relationship in between the at least two tumor-filled areas. The method further includes arranging an array of insulated electrode elements on the body of the patient. The array of insulated electrode element is coupled to a control device. The method further includes implementing at least two subarray firing configurations for the array of insulated electrode elements to treat the at least two tumor-filled areas depending at least in part upon the spatial relationship in between the at least two tumor-filled areas such that each subarray firing configuration treats a respective tumor-filled area.

The present invention in another form is directed to a method of delivering tumor treating electric fields to a body of a patient. The method includes scanning the body of the patient for identifying at least two tumor-filled areas. Each tumor-filled area has at least one tumor therein. The method further includes determining a spatial relationship in between the at least two tumor-filled areas. The method further includes arranging an array of insulated electrode elements on the body of the patient. The array of insulated electrode elements is coupled to a control device. The method further includes triaging the tumors in the at least two tumor-filled areas to obtain a triage strategy. The method further includes implementing at least two subarray firing configurations for the array of insulated electrode elements to treat the at least two tumor-filled areas depending at least in part upon the spatial relationship in between the at least two tumor-filled areas and the triage strategy such that each subarray firing configuration treats a respective tumor-filled area.

The present invention in yet another form is directed to a method of delivering tumor treating electric fields to a body of a patient. The method includes scanning the body of the patient for identifying at least two tumor-filled areas. Each tumor-filled area has at least one tumor therein. The method further includes determining a spatial relationship in between the at least two tumor-filled areas. The method further includes arranging an array of insulated electrode elements on the body of the patient. The array of insulated electrode elements is coupled to a control device. The method further includes determining at least two subarray firing configurations for the array of insulated electrode elements depending at least in part upon the spatial relationship in between the at least two tumor-filled areas. Each subarray firing configuration is configured for treating a respective tumor-filled area. The method further includes determining if the at least two subarray firing configurations are simultaneously implementable or sequentially implementable. The method further includes simultaneously implementing or sequentially implementing the at least two subarray firing configurations for treating the at least two tumor-filled areas.

The present invention in yet another form is directed to a method of delivering tumor treating electric fields to a body of a patient. The method includes scanning the body of the patient for identifying at least one tumor-filled area. Each tumor-filled area has at least one tumor therein. The method also includes arranging an array of insulated electrode elements on the body of the patient. The array of insulated electrode elements are coupled to a control device. The method also includes implementing at least one initial subarray firing configuration for the array of insulated electrode elements to treat the at least one tumor-filled area. The method further includes sensing temperatures of the insulated electrode elements of the array of insulated electrode elements. The method further includes implementing at least one alternative subarray firing configuration for the array of insulated electrode elements depending upon the sensed temperatures to treat the at least one tumor-filled area.

An advantage of the present invention is that the insulated electrode system and the method thereof may simultaneously treat multiple, spatially distant tumors, or clusters thereof, with two or more firing configurations using differing electrode elements.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1A:
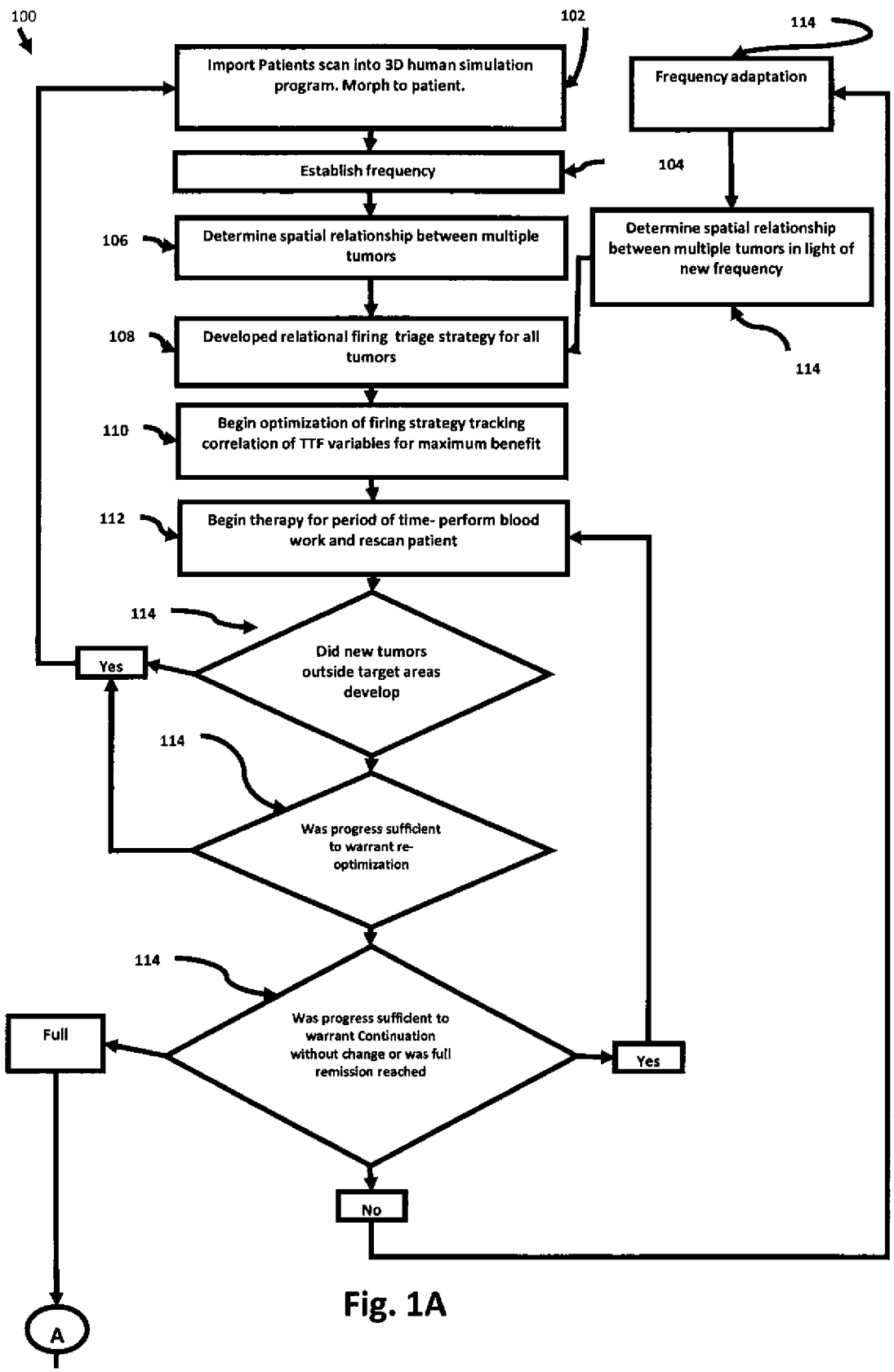
FIGS. 1A-1B illustrate a flowchart of a method for applying Adaptive Tumor Treating Fields.
Figure 1B:
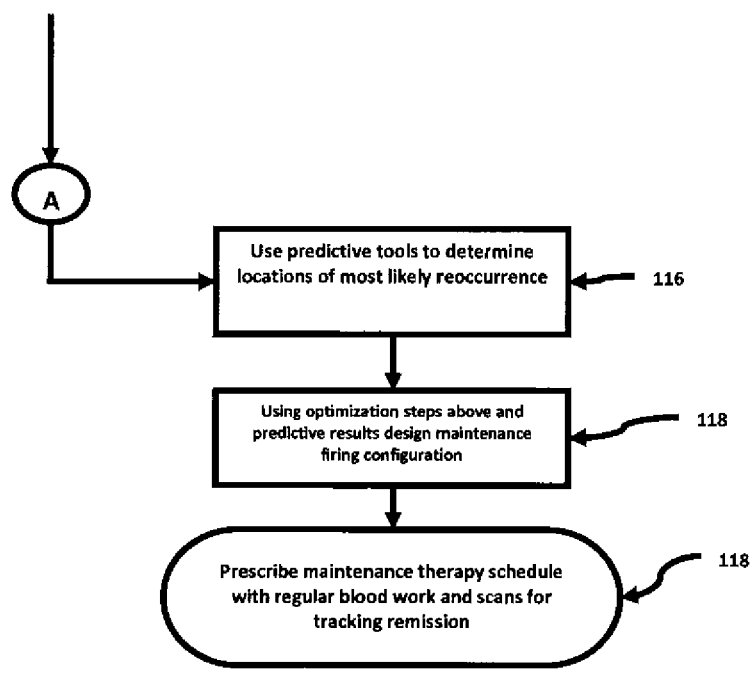

Referring now to FIGS. 1A-1B, there is shown a flowchart of an outline of the process for applying Adaptive Tumor Treating Fields (ATTF). The insulated electrode system may include a control device, an array of insulated electrode elements, a field generator, and one or more sensors for sensing the real-time temperature of the insulated electrode system. The insulated electrode system may also include a scanner, such as a 3D scanner. A multilayer flex circuit may couple the insulated electrode elements, the control device, and the field generator to one another. The control device may be programmed to send signals to the field generator, including the frequency range to be sent to the array electrode elements, as well as what array electrode elements are to be used in what firing configuration and sequence.

The control device may or may not perform certain steps of the methods described herein. For example, the control device may calculate or determine at least two subarray firing configurations for the array of insulated electrode elements. Alternatively, the control device may receive at least two subarray firing configurations from a 3D simulator. Therein, the control device may evaluate real-time system conditions and determine which preloaded firing configuration(s) may be implemented. Such a calculation may be dependent upon the spatial relationship between two or more tumor-filled areas, a triage strategy, a duty cycle of each insulated electrode element, a sensed temperature of each insulated electrode element, a peak power consumption of the array of insulated electrode elements, a total power consumption of the array of insulated electrode elements, a power availability of the field generator of the insulated electrode system, and/or a time constraint, for example 1 to 3 seconds between firing electric fields, to maintain the optimal therapeutic effect. The control device may determine the peak and/or total power consumption. For example, upon firing more electrode elements simultaneously, more power will be drawn from the field generator, and this power rating or total power limit of the field generator cannot be exceeded in any particular firing configuration. If the insulated electrode system is operating from battery power, the power limit may also be determined by the available battery life. The control device may track the time spent on battery power in order to alter the firing configuration.

As used herein, a tumor-filled area is a region of the body of the patient wherein one or more tumors reside. The tumor-filled areas may be spaced apart from one another at a distance such that a single electric field from a given firing configuration cannot be used to treat both tumor-filled areas. Thereby, the spatial relationship between the tumors or clusters thereof requires that two or more electrode elements be used to deliver an optimized therapeutic field to each of the tumors or clusters thereof.

The control device can implement the firing configurations simultaneously and/or sequentially throughout a treatment session. The control device may optimize the treatment process by simultaneously treating as many tumor-filled areas as possible. The control device may also assign a respective group of insulated electrode elements to each subarray firing configuration. The groups can be composed of differing electrode elements such that the groups do not share the exact same electrode elements. For instance, the groups may share some common electrode elements amongst themselves or the groups may be composed of completely different electrode elements.

The process of treating diffuse tumors may include scanning the body of the patient. The scanner may or may not be a component of the insulated electrode system. Hence, the control device may identify the tumors and their spatial relationship relative to one another. The control device may integrate the scan of tumors into a phantom to map locations. The control device may run firing simulations and/or mathematical algorithms to determine how many separate firing configurations are needed to create therapeutic fields that optimally treat the tumor-filled areas. The control device may then triage the tumors or clusters thereof. The control device may also determine which tumor or cluster thereof can be treated together with a single disk firing configuration, treated with separate firing configurations applied simultaneously, and/or treated with separate firing configurations applied sequentially. The control device may incorporate any desired limiting characteristic in determining the firing configuration. For instance, the control device may incorporate target array element duty cycles and/or limits on power available from the field generator. Alternatively, the control device may receive information regarding the tumors, e.g. the spatial relationship and a triage strategy thereof. For instance, the control device may receive and store the position(s) of the tumor(s), the firing configurations, the triage strategy, etc., which may be predetermined by a simulator and/or medical professional.

The control device may also optimize the total therapy plan. For instance, the control device may determine which firing configurations should be included in each therapy session (i.e. which tumors will be treated every day) and which tumors will be treated on a less frequent schedule to optimize overall TTF therapy. It may not be possible or necessary to treat every tumor or cluster thereof in every firing sequence due to tumor location(s), heat generation, power consumption, triage strategy, etc. The control device may optimize the overall therapy to the patient for their entire situation, and thereby accordingly adapt or alter the treatment plan as the situation changes. Advantageously, the array(s) of insulated electrode elements can be placed on the body of the patient every time, but the software of the control device varies the treatment, e.g. reconfigures the firing configuration(s) of the independently programmable electrode elements, in order to optimize the treatment session(s). For example, firing configurations and sequences can over the course of a day, or vary from one day to the next as some tumors may be treated every time and some may get treatment less frequently on some days during the week or month depending on the factors listed herein, the results seen in body scans, blood work, etc. A total plan can be developed that varies by hour, day, time of day (sleeping vs awake time), week, month based all the previously noted parameters. Another way to optimize the total therapy plan may include treating lower priority tumors in between periods where the temperature of the electrode elements used to treat higher priority tumors need to cool down. In other words, the downtime of overheating array elements in a first, e.g. higher priority, group may allow the use of other array elements in a second, e.g. lower priority, group to be used to treat lower priority tumors that allow the high priority disks to cool in temperature.

3D Simulations: Scans (CT scans, MRI's, etc.) of a patient showing the location of their disease is loaded into a 3D simulation program that uses finite element method or other physics solvers to determine the characteristics of an electric field through the human body (at block 102). Such programs use mathematical algorithms, phantoms, or avatars to simulate the patient. The phantom chosen to closely match a patient can then be morphed to further match the size of the patient. By using one or more 2D or 3D D scans of a patient (CT Scans, MRI's, etc.), tumor locations can be accurately determined, as well as their spatial distance relative to each other by being imported into the simulator. It should be appreciated that the control device may or may not include a simulation program.

Establish Frequency: Biopsies of the patient's tumor(s) are used to determine absolute average cell size of the cancer. In the event a biopsy is not available database knowledge of cell size by cancer type is used to reference the cell size of the type of cancer. The most effective frequency for the patient's cancer is chosen based on cell size. This step may be repeated if initial therapy is not successful (at block 104).

Spatial Relationship of Tumors: Using the 3D simulation, the spatial relationship of multiple tumors to each other, relative to the variables of tumor treating fields is established. For example, an advanced patient may have 14 distinct tumors. The following types of questions are asked and answered through running simulations (at block 106). This step may be repeated if initial therapy is not successful. It should be appreciated that the spatial relationship of the multiple tumors may or may not be determined by the control device. For instance, the control device may receive a predetermined spatial relationship which is calculated by a 3D simulation.

Are any of the 14 tumors clustered together to the point that the cluster could be treated by one firing configuration (Firing configuration is a sequence of tumor treating fields delivered over a given area, from different angles, frequencies, and timings)? Or do the tumors require 14 separate and distinct firing sequences.

Are any of the tumors or clusters of tumors, far apart on the body, indicating that 2 electric fields may be used at the same time with minimal interaction between the 2 fields?

Are the placement of the tumors such that the duty cycle of array electrode elements will not be taxed to overheating, enabling all tumors to be treated from the start. Or do the tumors have to be triaged and treated in priority sequence. Some now some later as early treated tumors are eliminated or brought under control.

Does the placement of tumors require special firing configurations such as co-planner fields or uneven array pairs?

Additional similar questions will be answered.

Triage Strategy: In the example above, once the spatial relationship between tumors is understood, the tumors may be triaged in order to obtain a triage strategy. The triage strategy outlines which tumor(s) should be treated more than other tumor(s). Each tumor or clusters of tumors must be graded or assigned a priority value by how life threatening they are to the patient. If some tumors are particularly life threatening. They will be prioritized. Since adding additional firing sequences from different angles over the same area has been shown to speed up tumor reduction, high priority tumors will receive more angles of delivery. This may mean lower grade tumors that are less life threatening may have to wait to receive therapy until the more threatening tumors are resolved. This step may be repeated if initial therapy is not successful (at block 108). It should be appreciated that the control device may or may not determine the triage strategy. For instance, the control device may receive a triage strategy which is determined by a medical professional. Additionally, for instance, the control device may determine, solely or in tandem with a medical professional, the triage strategy by ranking the tumors according to one or more characteristics. After one or more rounds of therapy, the control device and/or medical professional may re-triage the tumors to obtain an updated triage strategy. Hence, the triage ranking of tumors may change over time as new information is gained such as relative growth, growth vs expectations, new tumors, success rates, patient compliance, etc. The control device and/or medical professional may reprioritize treatment via the array firing configurations during or over several therapy sessions.

Interactive Optimization Process: Based on the spatial relationship between tumors, and the triage grade of each tumor, an initial firing sequence will be designed. The initial firing sequence is then optimized using 3D simulations. Optimization considers all variables that contribute to the effectiveness of therapy and their interaction with each other. Optimization occurs for every firing angle and considers the duty cycle of array electrode elements overall, as firing sequences occur (at block 110).

For example, the primary frequency for a cancer type may have been determined to be 150 kHz, with an optimal intensity of 2.5 V/cm through the targeted tumor. This combination of frequency and intensity may prove achievable for the first angle of delivery. However, the $2^{nd}$ angle of delivery may show a drop-in intensity to 1.5 V/cm, less than optimal. This is because the travel path of the $2^{nd}$ angel may be a different distance and may travel through different organs. The optimization process then begins testing alterations in frequency and power output to see if the optimal intensity can be achieved for the $2^{nd}$ angle. For example, the frequency may be changed to 140 kHz or to 160 kHz. These relatively modest adjustments in frequency may raise the intensity back to the desired 2.5 V/cm because frequency makes a difference in intensity when traveling through organs with different dielectric constants. This would represent an optimization because it is believed that maintaining intensity is more important than modest fluctuations in frequencies.

In a similar fashion, the optimization process would test whether increasing the power output on the $2^{nd}$ firing could be done without raising the array electrode element temperatures above safety levels. Suppose it is determined that raising power levels is successful at maintaining intensity at 2.5 V/cm but does raise array electrode element temperatures above desired levels. The optimization process would then begin testing lowering the duty cycle of array electrode elements in order to preserve the new power levels without raising temperature. Final optimization must require that all targeted tumors are exposed to an electric field at the optimized frequency and intensity every 1 to 3 seconds.

The above are just some of the examples of how the optimization process takes into account how all the variables of electric field therapy interact with each other to produce the optimum firing sequence. This results in the most effective therapy for treating multiple tumors. It should be appreciated that all variables are not outlined here but are included in the interactive optimization process.

Once electric field therapy begins the adaptive process requires regular blood draws to look for tumor markers and regular scans to see if changes that require adaptation have occurred 112.

This close monitoring determines whether therapy should continue without changes or whether adaptations are needed. Adaptations may be made for both positive and negative results. If negative results are made, new biopsies may be requested to see if frequencies should be changed. Or if new cancer has broken out, re-optimization may be needed. If successful results are observed, low priority untreated tumors may now be brought under therapy 114.

Predictive tools to guide preventing therapy: Once remission or significant improvement is observed, the use of predictive tools are used to develop a preventative therapy plan. The predictive tools determine the most likely area of the next reoccurrence, such as the lungs, liver, peritoneal cavity, etc. The predictive tools work in many ways. Some use genetic markers gathered through blood work or biopsy. Some use aggregated databases from large numbers of cancer patients with different types of disease. Statistical probabilities and algorithms are used to predict the most likely area of reoccurrence. Other predictive tools not mentioned can be used as well (at block 116).

Once a likely area of reoccurrence is determined an initial preventative firing sequence is developed. The initial firing sequence is then put through the above optimization process. The process determines the optimal firing sequence for preventive therapy. Preventive therapy is scheduled which may vary depending on the patient and the severity of their disease. Prevention could range from alternating periods (e.g. on one month, off two months), or annual, bi-annual or quarterly prescriptions. Regular blood work tracking tumor markers and scans are done to monitor the preventative therapy. If needed adjustments are prescribed or the entire optimization process repeated. Maintenance therapy may also include sweeps through the body in previously unaffected areas to remove undetectable tumors (at block 118).

Figure 2:
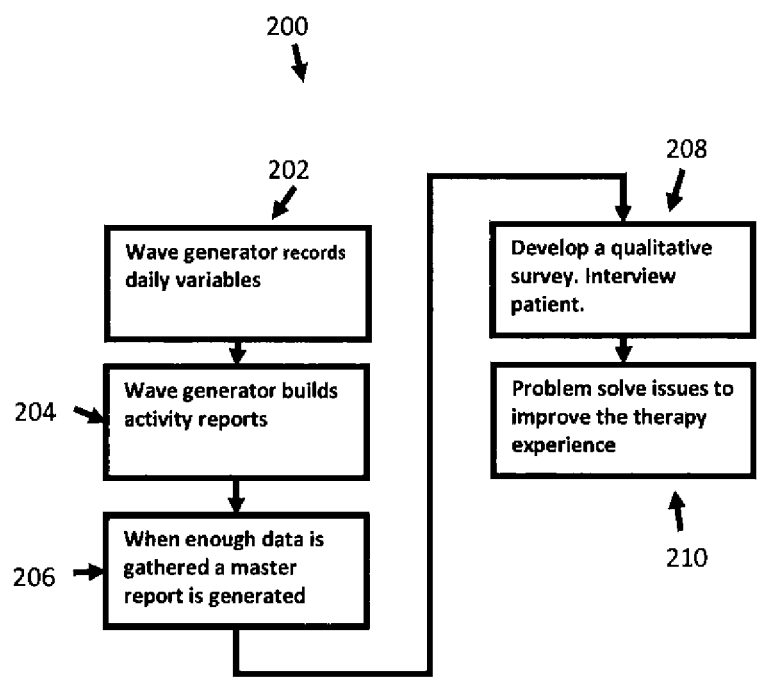
FIG. 2 illustrates a flowchart of a method for increasing patient compliance.

Patient Compliance: It is well known that the success of electric field therapy is highly dependent on patient compliance. Electric field therapy is an on-off therapy. That is while it is on, it is working, when it is turned off its therapeutic benefits stop. Patient compliance has been documented to be high, but improvement is needed. The process 200 can be constantly run to increase patient compliance (FIG. 2). The control device, e.g. wave generator, may record the daily variables (at block 202). The control device may also build activity reports (at block 204). Thereafter, a master report can be generated (at block 206). Then, a survey may be developed and the patient may be accordingly interviewed regarding the therapy experience (at block 208). If issues exist, the process 200 may include problem solving the issues to improve the patient's therapy experience (at block 210).

Figure 3A:
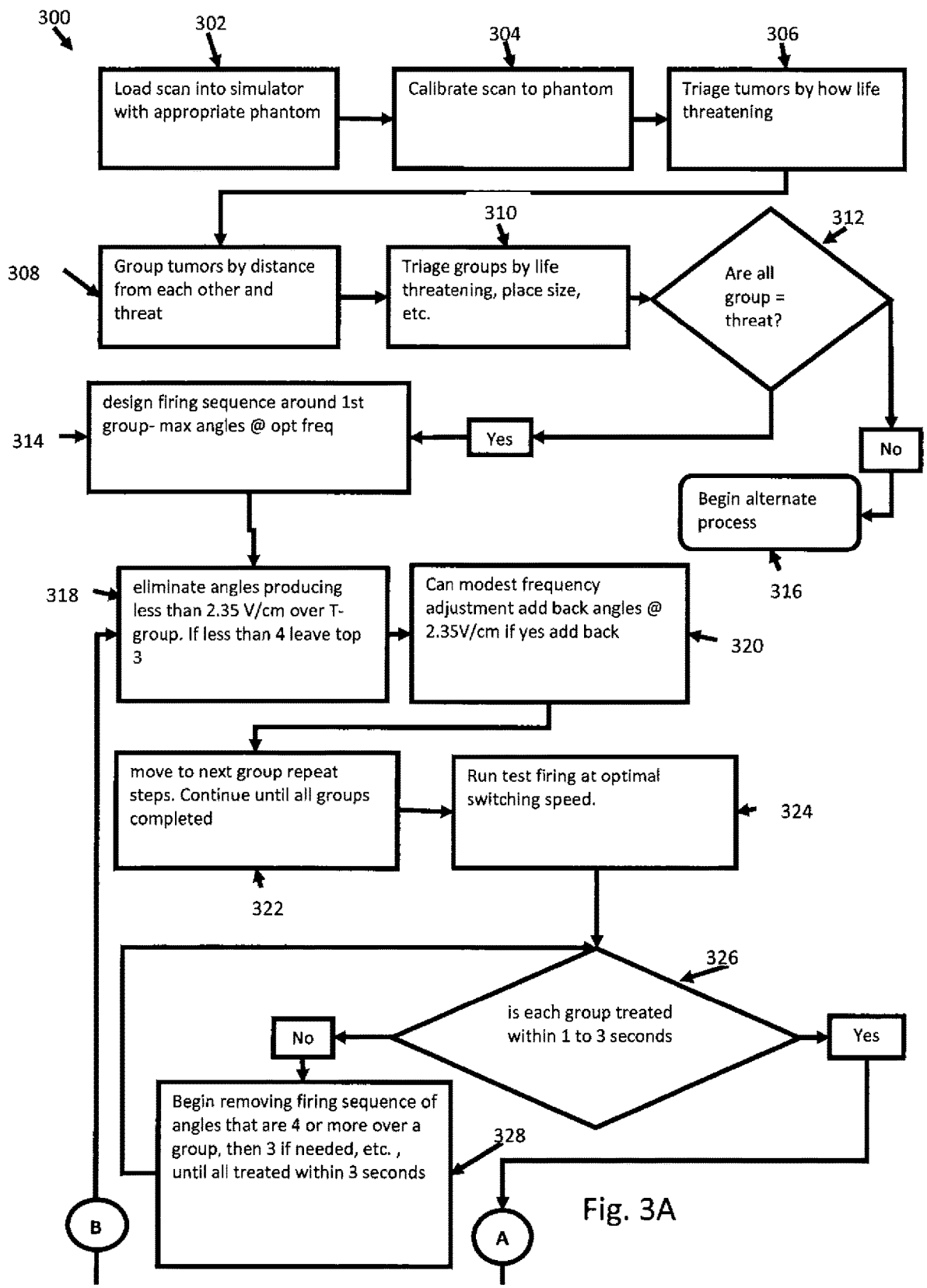
FIGS. 3A-3C illustrate a flowchart of a method for optimizing electric field therapy when all tumors are of an equal threat.
Figure 3B:
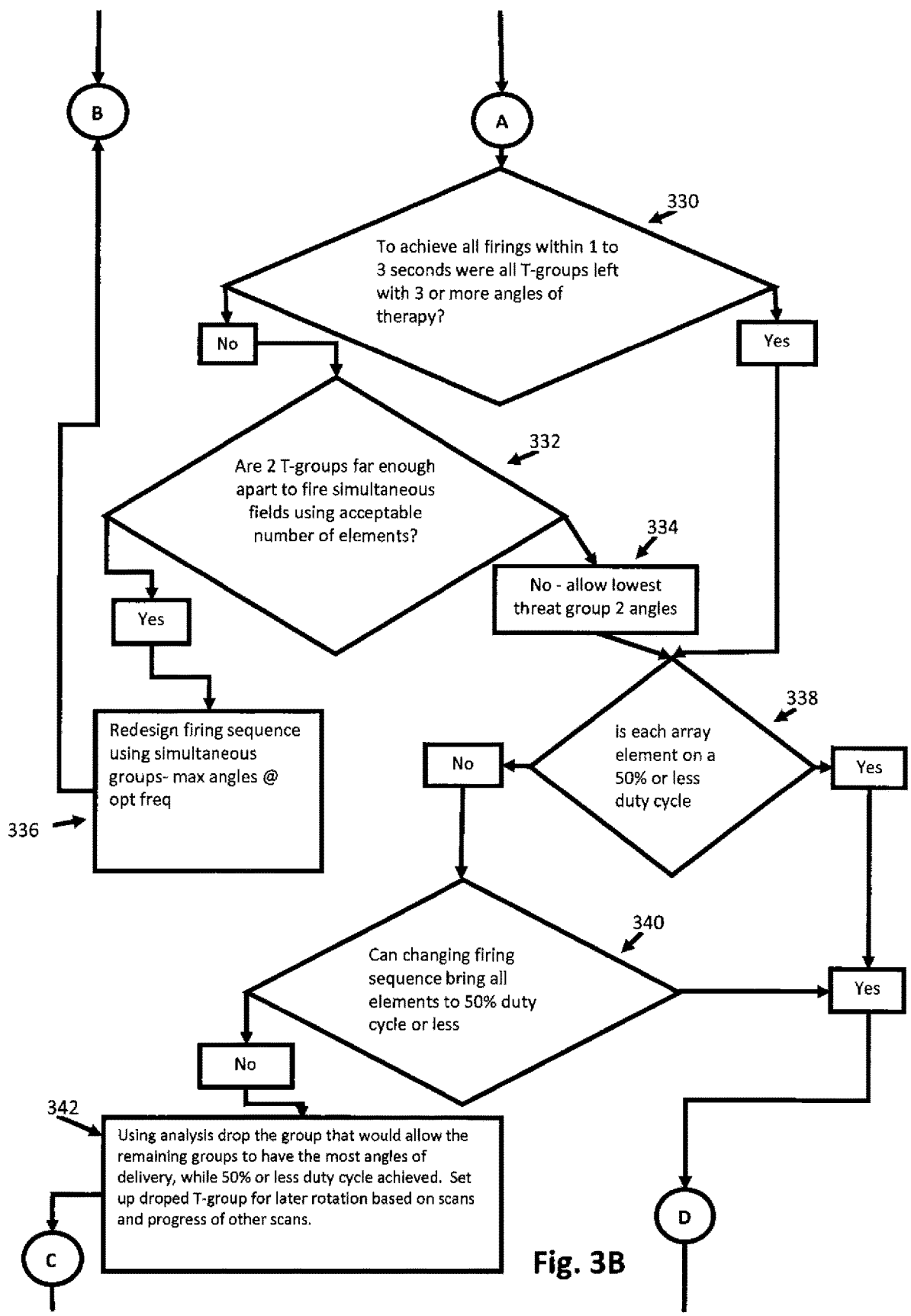
Figure 3C:
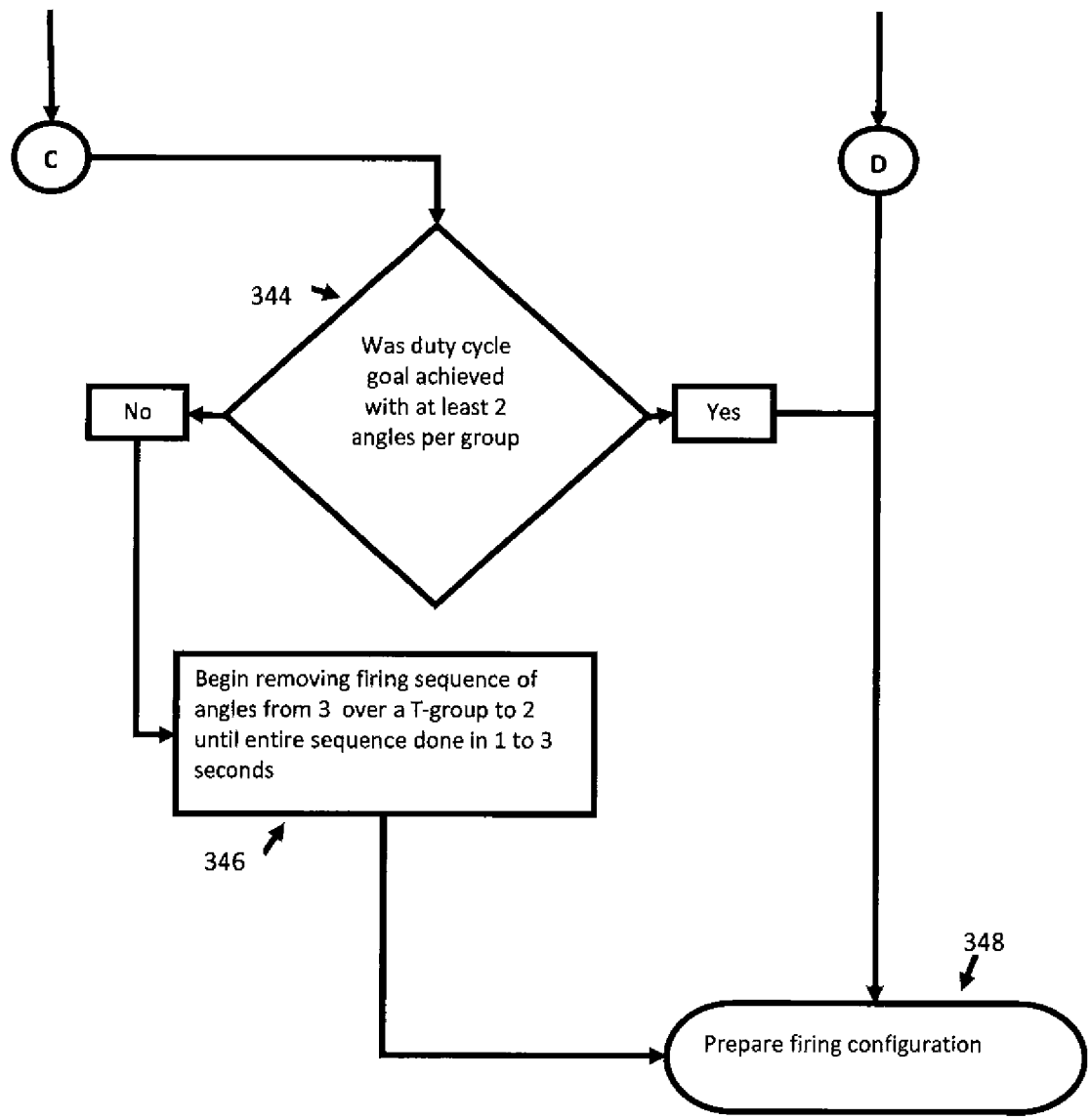

In yet another invention, optimization of electric field therapy is prioritized when all tumors or tumor groups (T Groups), are of equal threat. In such a case, it may be that inclusion and optimization of all T groups using a 50% duty cycle of array elements, and with each T group being treated within 1 to 3 seconds, is not possible. In such a case a T group is selected to be dropped from therapy based on how its absence will enhance the optimization of the other T groups that will remain in therapy (FIGS. 3A-3C).

The method 300 may include loading a scan into a simulator (at block 302). The scan may be calibrated to the phantom (at block 304). The tumors can be triaged (at block 306). Then, the tumors may be grouped by distance and the triaged strategy (at block 308). Then, the groups of tumors may be triaged (at block 310). Thereafter, it may be queried whether the groups of tumors are of an equal threat (at block 312). If yes, firing sequences may be accordingly designed (at block 314). If no, an alternative process may be started, such as the method 400 (at block 316). The method 300 may then include eliminating firing angles which produce less than 2.35 V/cm (at block 318). If modest frequency adjustments can add back angles at 2.35 V/cm, then such angles will be added back (at block 320). Then, the aforementioned steps 318, 320 will be repeated for all of the groups of tumors (at block 322). A test may then be run at the optimal switching speed (at block 324). It may then be queried whether each group is treated within 1 to 3 seconds (at block 326). If no, certain firing sequences may be removed (at block 328). If yes, it may then be queried whether all remaining T-groups have three or more angles of therapy (at block 330). If yes, the method 300 may continue by determining a duty cycle characteristic (at block 338). If no, it may be queried whether two T-groups are sufficiently spaced apart to fire simultaneous fields (at block 332). If no, the method 300 may allow the lowest threat group two angles (at block 334). If yes, firing sequences using simultaneous groups may be redesigned (at block 336). If each array element has a 50% or less duty cycle, the firing configuration may be prepared (at block 348). If each array element does not have a 50% or less duty cycle, the method may determine whether changing the firing sequence will lower the duty cycle (at block 340). If yes, the firing configuration may be prepared (at block 348). If no, then the group that would allow the remaining groups to have the most angles of delivery, while still being under 50%, may be dropped (at block 342). The method 300 may then query whether the duty cycle goal was achieved with at least two angles per group (at block 344). If yes, the firing configuration may be prepared (at block 348). If no, then certain firing sequences may be removed (at block 346). Thereafter, the firing configuration may be subsequently prepared (at block 348).

Figure 4A:
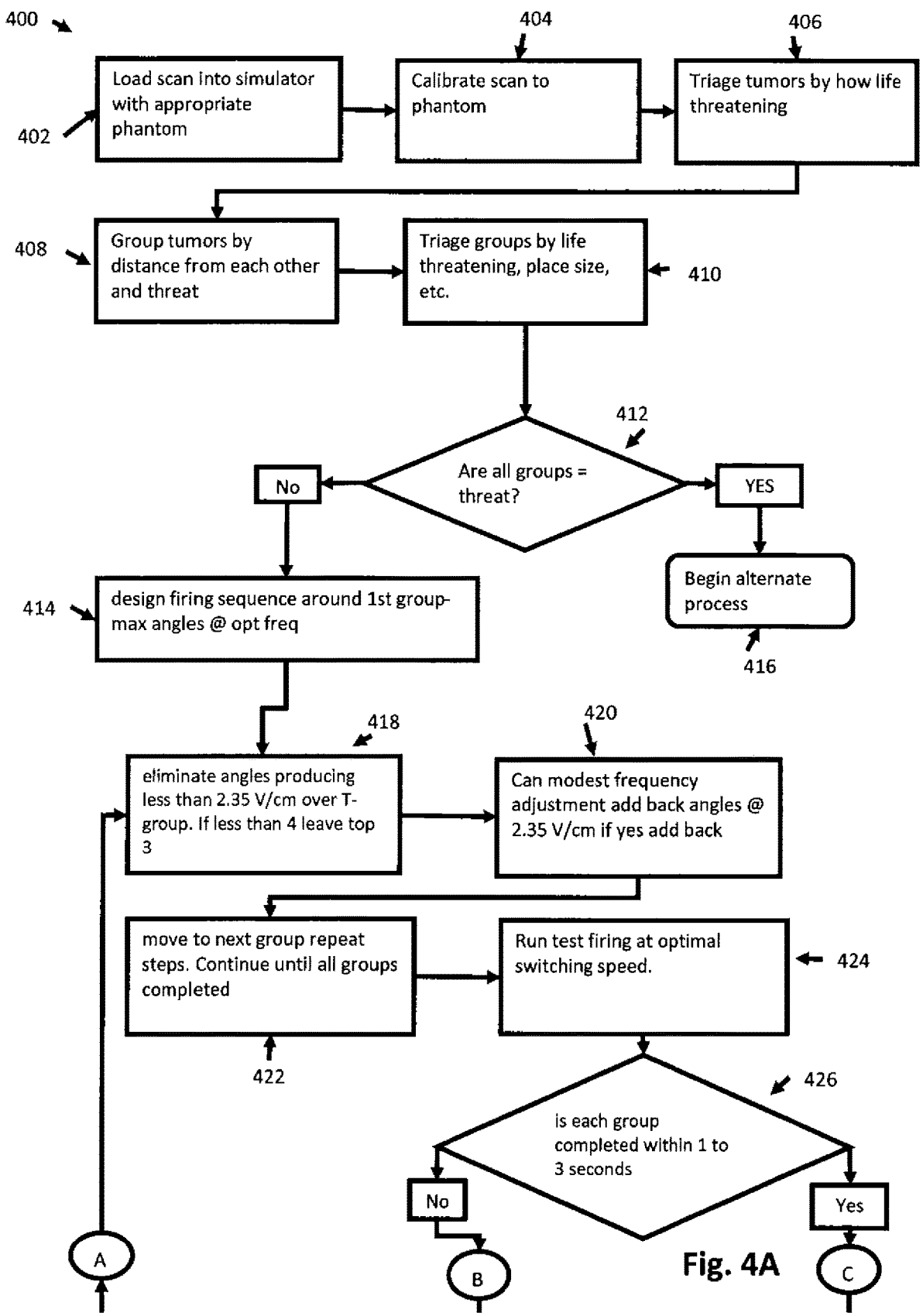
FIGS. 4A-4C illustrate a flowchart of a method for optimizing electric field therapy when all tumors are not of an equal threat.
Figure 4B:
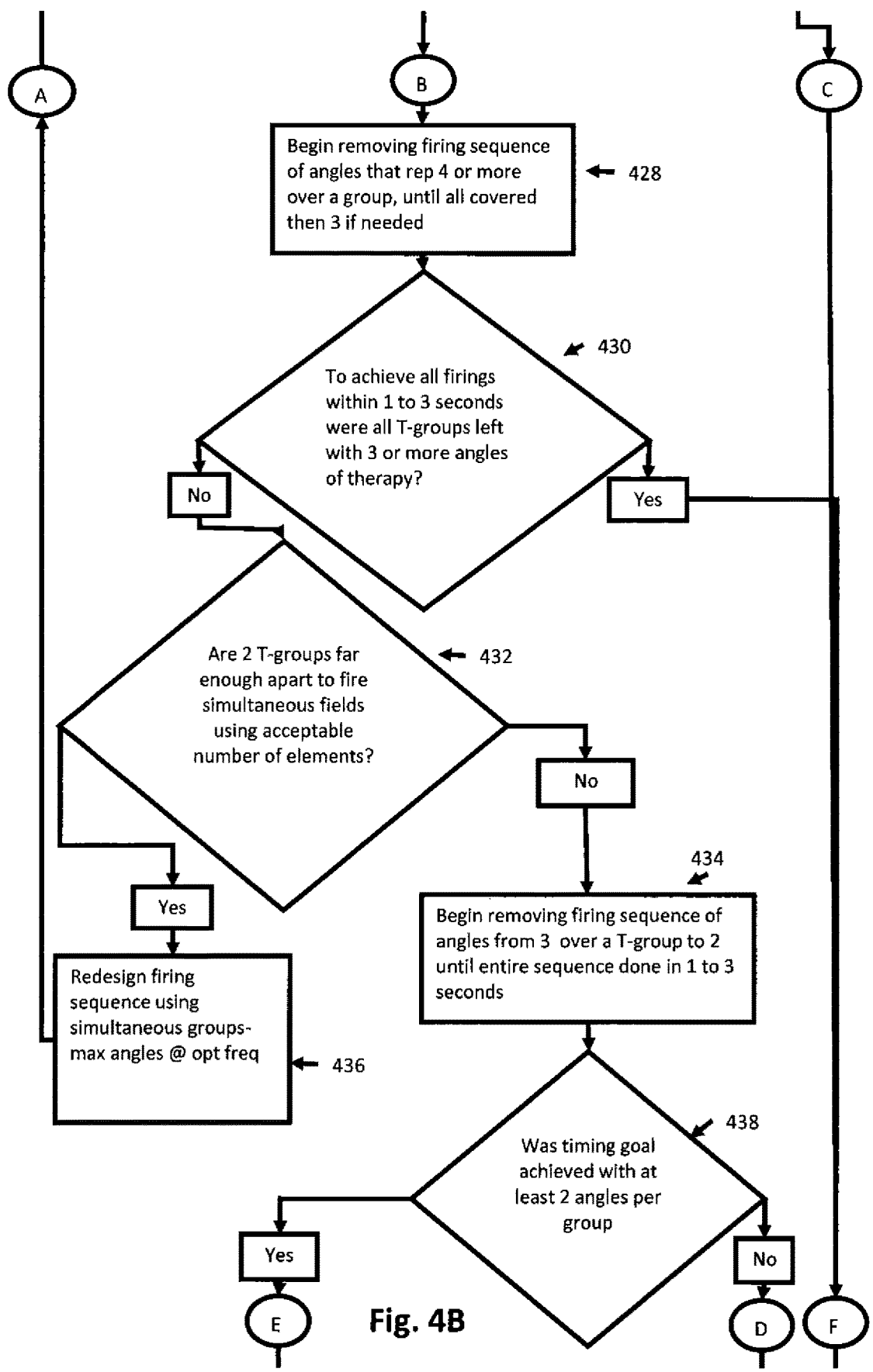
Figure 4C:
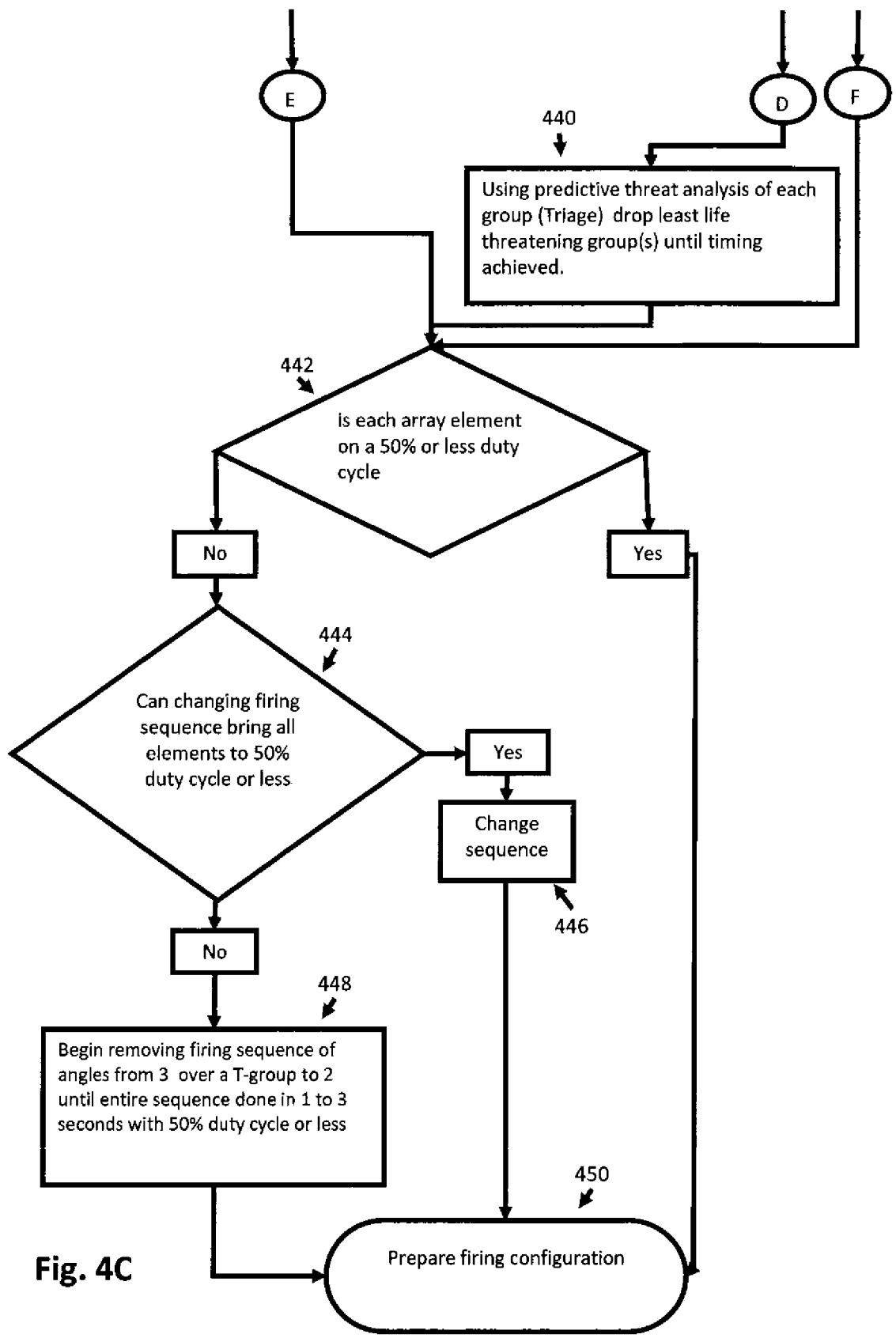

In yet another invention, optimization of electric field therapy is prioritized when all tumors are not of equal threat. In such as case, it may be that inclusion and optimization of all T groups using a 50% duty cycle of array elements, and with each T group being treated within 1 to 3 seconds, is not possible. In such a case a T group is selected to be dropped from therapy based on how life threatening it is compared to other T groups (FIGS. 4A-4C).

The method 400 may include loading a scan into a simulator (at block 402). The scan may be calibrated to the phantom (at block 404). The tumors can be triaged (at block 406). Then, the tumors may be grouped by distance and the triaged strategy (at block 408). Then, the groups of tumors may be triaged (at block 410). Thereafter, the method 400 may query whether the groups of tumors are of an equal threat (at block 412). If no, firing sequences may be accordingly designed (at block 414). If yes, an alternative process may be started, such as the method 300 (at block 416). The method 400 may then include eliminating firing angles which produce less than 2.35 V/cm (at block 418). If modest frequency adjustments can add back angles at 2.35 V/cm, then such angles will be added back (at block 420). Then, the aforementioned steps 418, 420 will be repeated for all of the groups of tumors (at block 422). The method 400 may then run a firing test at the optimal switching speed (at block 424). It may then be queried whether each group is treated within 1 to 3 seconds (at block 426). If yes, the method 400 may continue by determining a duty cycle characteristic wherein the method 400 determines whether each array element has a 50% or less duty cycle (at block 442). If no, certain firing sequences may be removed (at block 428). Then, the method 400 may query whether all remaining T-groups have three or more angles of therapy (at block 430). If yes, the method 400 may continue with step 442. If no, it may be queried whether two T-groups are sufficiently spaced apart to fire simultaneous fields (at block 432). If no, the method 400 may remove the firing sequence of angles from three to two until the entire fire sequence can be done in 1 to 3 seconds for a given group of tumors (at block 434). If yes, the method 400 may redesign the firing sequence using simultaneous groups with maximum angles at the optimum frequency (at block 436). After the method 400 has removed certain firing sequences in step 434, the method 400 may query whether the timing goal of 1 to 3 seconds can be achieved with at least two angles per each group of tumors (at block 438). If yes, the method 400 may continue to step 442. If no, the method 400 may drop the least life-threatening groups until the timing goal is achieved (at block 440). In order to determine which groups should be dropped, the method 400 may incorporate a triage strategy of current tumors and/or a predictive threat analysis. Then, the method 400 may continue to step 442 to determine whether each array element has a duty cycle of 50% or less. If each array element has a 50% or less duty cycle, the firing configuration may be prepared (at block 450). If each array element does not have a 50% or less duty cycle, the method 400 may determine whether changing the firing sequence will lower the duty cycle (at block 444). If yes, the sequence may be changed (at block 446). Thereafter, the firing configuration may be prepared (at block 450). If no, then the method 400 may begin removing the firing sequence of angles from three to two until the entire sequence may be accomplished in 1 to 3 seconds with a 50% duty cycle (at block 448). Thereafter, the method 400 may continue to step 450 to prepare the firing configuration.

In yet another invention, the daily therapy of the electric field is begun at low power and slowly ramps up, giving the patient time to adjust.

In yet another invention, the wave generator contains wireless and/or remote monitoring/reporting, re-programming, or updating of the system via wireless modem. This could include cellular, Wi-Fi, Bluetooth, or other wireless technologies.

In yet another invention, array elements are fitted or changed with different characteristics to increase efficiency based on frequencies used.

In yet another invention, a process for minimizing peripheral nerve stimulation (PNS) is used. Test arrays are placed on a patient. Power levels are slowly adjusted upwards to determine locations on the patient that are susceptible to PNS. Those areas susceptible to PNS are loaded into 3D simulators. Areas sensitive to PNS are avoided when designing firing configurations. Compensating firing configurations are designed.

The present invention is made up of a master array of insulated array elements placed on the patient's body. The master array is made up of individual insulated array elements. Each array element is computerized. Each array element has its own unique address. The master array is divided into subarray pairs that are made up of 2 or more array elements that are energized together in order to deliver low frequency electric fields through the body. These fields have been shown to reduce cancer tumors. The subarray elements are software configured to energize in an advantageous sequence based on treatment simulations performed for each patient. However, an initial subarray configuration can be overridden by the introduction of alternative configurations that are activated based on variables affecting the subarray elements (temperature, adhesion, voltage, faults, etc.) and from the real-time monitoring of patient conditions, as well as the result of actions taken the patient or caregivers that affect beneficial subarray configuration during therapy. For instance, the control device may select initial firing configurations and subsequently reselect alternative firing configurations based upon real-time conditions. This is done to optimize beneficial therapy for the patient. Additionally, the control device may select alternative firing configurations which are optimized to treat potential tumor areas based upon a preventive therapy regimen.

Definitions:
1. Subarray Configurations: The lifebridge system utilizes output from an external numerical computational model which simulates the human body using a wide range of physical and electrical (size, tissue type, organ placement, thermal, electrical) characteristics. These characteristics enable Lifebridge 10000 to simulate the effects of a number of array element subarray configurations. These simulations inform the assignment of subarray configuration variables:
    a. Addresses of array elements energized together
    b. Phase assigned to each array element address or group of addresses
    c. Voltages applied to each array element or group of addresses
    d. Sequence each array or group of array elements is energized
    e. Duration each array or group of array elements is energized
    f. Frequency each array or group of array elements operates. Note, there may be time periods where no array elements are energized.
2. Adaptive Tumor Treating Field: Arrays in a subarray are energized together so that they form the desired therapeutic field over the target area. Array elements can be dynamically (adaptively) reassigned to new subarray configurations as determined by the lifebridge 10000 system algorithms.

3. Adaptive Optimization: results in a more optimal subarray configuration, subarray sequence, subarray duration, determined by a combination of weighted values for therapeutic field delivery and duty cycle of an array element for a given state of subarray elements (current temperature, expected voltage versus measured voltage, communications status, etc.). The control device can determine if each electrode element is in one of the following zones and thereafter conduct a corresponding temperature process to optimize the insulated electrode system.
4. Blue Zone: a temperature measurement value materially below those of neighboring array elements.
5. Green Zone: a temperature measurement value for an array element that is within acceptable range that requires no change to initial subarray configuration values
6. Yellow Zone: a temperature measurement value above green zone values, but below red zone values. The yellow zone will have 2 to 25 increments. These increments will be used to differentiate the absolute and direction of change (increasing or decreasing) for array element temperatures.
7. Red Zone: a temperature measurement value at or above a temperature for which the element will be de-energized and cannot be reenergized until measured temperature is within the values assigned to the yellow or green zone by the lifebridge 10000 system.
8. System Controller or Control Device: a control system for implementing tumor treating electromagnetic fields by way of independently and/or individually controlling the electrode elements. The control system may consist of computational and storage elements contained in the Lifebridge 10000 system. The elements may be located in the electrical systems physically integrated in to the wave generator, and/or connected to the wave generator via external communications port, and/or computer or mobile device and may be fully or partially located in a server or cloud service. Some or all system control functions will be carried out in a distributed computing environment. The control system or device may include a wave generator, a simulator, and/or a controller with a memory.

According to an aspect of the present invention, the controller, or more particularly the software within the memory of the controller, may or may not perform the following procedures:

Determining Subarray Configuration Procedure Overview: 1) Data and images, such as found in MRI, x-ray or other medical imaging, are entered into a medical numerical computational model that creates a "phantom" torso with the cancerous tumors located in a similar location as found in the patient. 2) Various simulations are run to determine the optimal array element energizing program. This program determines which array elements are energized, in what order, at what voltage and for what duration for every step in the system therapy program. This creates the subarray configuration list. Arrays that are energized in a given time period (typically from 0.5 to 3 seconds) are assigned to the same subarray for that time period in the program. 3). The subarray configuration program is then loaded into the system controller (i.e. Wave Generator).

Figure 5:
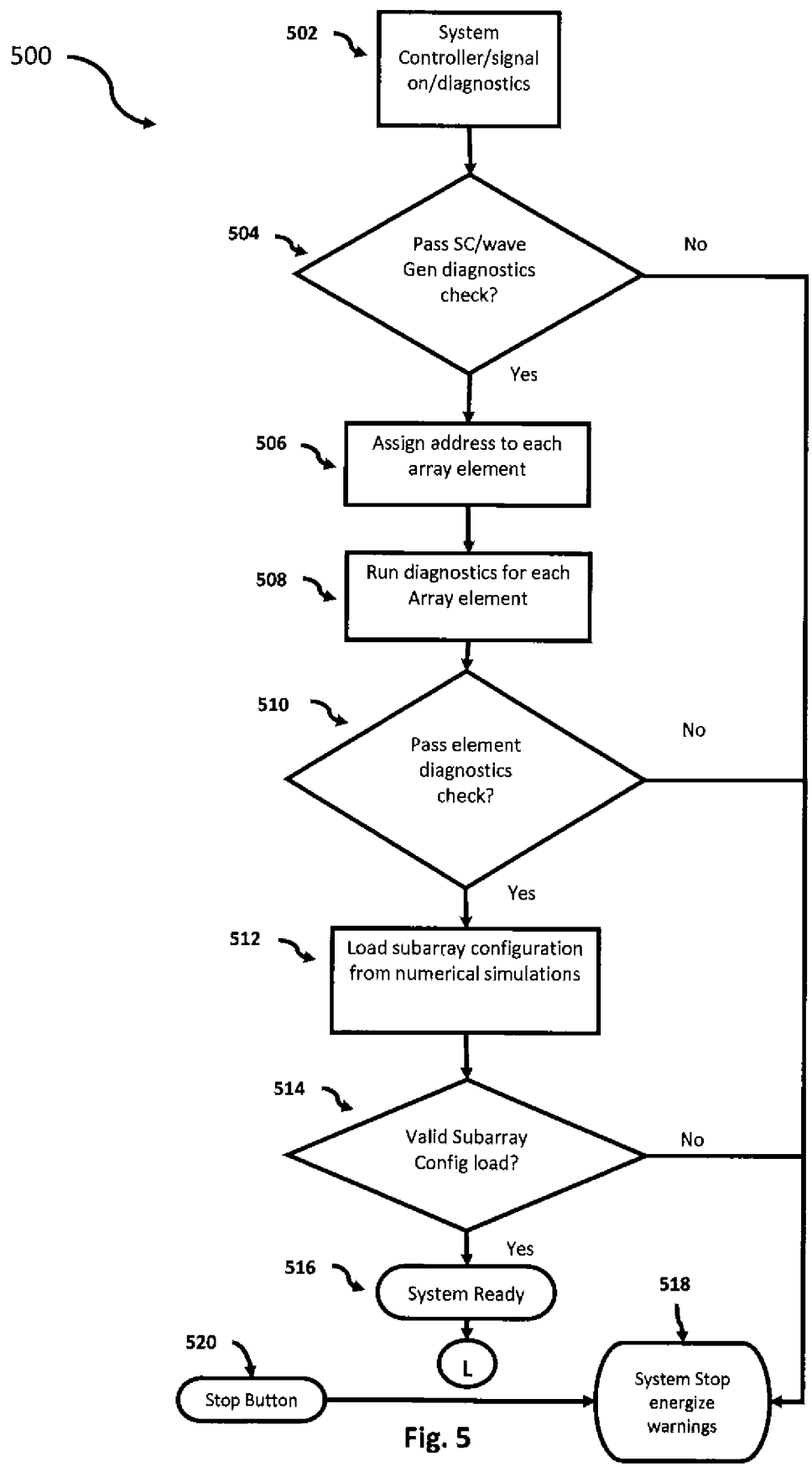
FIG. 5 illustrates a flowchart of a method for a configuration procedure of the system.
Figure 6:
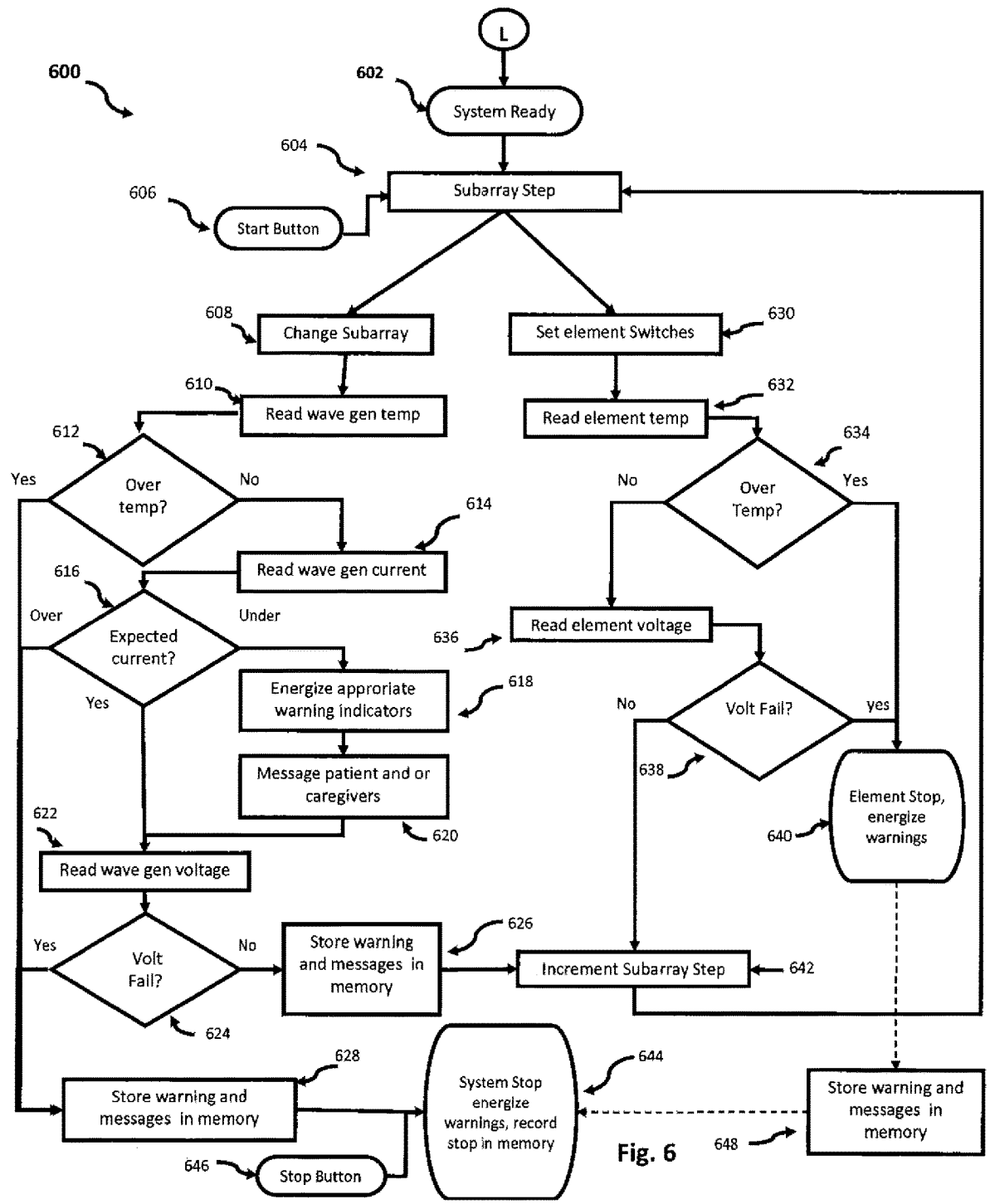
FIG. 6 illustrates a flowchart of a method for an operational procedure of the system.

The method 500 describes the Lifebridge 10000 System Configuration Procedure (FIG. 5). Initially, the System Controller (SC) is activated with a power switch and runs a self-diagnostic and hardware check. This includes temperature, current, voltage, communications ports, valid program load, system ID operation authorizations, etc. (at block 502). If SC passes a diagnostics check (at block 504), then continue to the next step. If a fault is found, the system will stop its start-up sequence, store the diagnostic values in the memory for immediate and/or delayed reporting to local and/or remote computer or mobile databases/displays. The software will trigger a local warning indictor and/or voice or tone (at block 518). Once diagnostics are checked and all values in acceptable ranges, the SC assigns a unique software address to each master array element physically and/or slave array element logically present in the system (at block 506). The SC then runs a diagnostic sequence with each array element (at block 508). This diagnostic check for program load, voltage, temperature sensor status, relay machine state (open or closed), etc. If elements pass diagnostics check then continue to the next step (at block 510). If a major fault is found the system will stop its start up sequence, store the diagnostic values in the memory for immediate and/or delayed reporting to local and/or remote computer or mobile databases/displays. The software will trigger a local warning indictor and/or voice or tone (at block 518). If no major fault is found, the SC will load the array energizing program (subarray configuration) into the memory of each array or master array(s) if a master/slave arrangement is appropriate for the given physical and/or logical array element arrays (at block 512). The program stored in the array elements is then validated against the master copy of the program via a checksum, hash, or other bit perfect validation method (at block 514). If a fault is found the system will stop its start-up sequence, store the diagnostic values in the memory for immediate and/or delayed reporting to local and/or remote computer or mobile databases/displays. The software will trigger a local warning indictor and/or voice or tone (at block 518). If array program load is validated by SC, the SC places the Lifebridge 10000 system in System Ready state (at block 516). If at any time during this sequence the stop button is activated (at block 520). The system will stop its start-up sequence, store the event in the memory for immediate and/or delayed reporting to local and/or remote computer or mobile databases/displays. The software will trigger a local warning indictor and/or voice or tone (at block 518).

The method 600 describes the Lifebridge 10000 System Operational Procedure (FIG. 600). The system is in a ready state (at block 602). A start button or switch 606 is physically engaged on the SC to start the execution of subarray configuration sequence step (at block 604). The SC communicates the start of the subarray sequence to all of the arrays (at block 622) and wave generator (at block 608), which set appropriate wave generator parameters and element phase, controlled by the element switches. Wave generator diagnostics are performed by the SC while the system subarray program is running (at blocks 610-624). If an under-current condition is found in the wave generator (i.e. below expected current values) the SC will energize warnings and alter patient and caregivers that array elements may not be adhered to patient sufficiently (at blocks 618-620). If diagnostics finds a major fault (over-temperature, over-current, over-voltage, etc.) in the wave generator the system will stop, store the diagnostic values in the memory for immediate and/or delayed reporting to local and/or remote computer or mobile databases/displays. The software will trigger a local warning indictor and/or voice or tone (at block 644). Concurrently, array element diagnostics are performed by the array elements and/or SC while the system subarray program is running (at blocks 632-638). If diagnostics finds a fault in an array element or group of array elements, the program will stop the elements, store the diagnostic values in the memory for immediate and/or delayed reporting to local and/or remote computer or mobile databases/displays (at block 640). Depending on the severity and type of array element fault, the SC may energize additional warnings and notifications and perform a system stop and activate appropriate warnings (at block 644). The response of the system is adaptive to the severity of the fault and the system determines fault handling procedures based on a set of algorithms. If no faults are detected during the execution of a subarray configuration, the system program will issue a "step subarray" at a time increment as determined by system program (at block 642). This will continue until the following conditions occur: the stop button/switch is engaged (at block 646), a SC wave generator diagnostic fault is detected (under/over voltage, under/over temperature, under/over current, array communications fault) (at blocks 612-628), or an array fault is detected (under/over voltage, under/over temperature) (at blocks 632-638).

In addition to the method 600, as discussed above, the Lifebridge 10000 System may have enhanced procedures for handling temperature measurements to optimize delivery of therapy. The generation of tumor treating fields creates some heating of the array elements due to the creation of an alternating electric field through the patient. Some heat is also generated by the circuitry on the array as well as resistance in the wires and other resistive elements. While some degree of heating is expected, heating which causes the temperature of the element and patients' skin to exceeded 105 F is not acceptable.

Further, the temperature of the elements is monitored, so that appropriate mitigating steps are taken to minimize, stabilize or reduce the heat generated in an element, thereby slowing or stopping the temperature rise of the element and patient's skin before it reaches an unacceptable temperature. Therein, the control device may monitor the temperatures of the electrode elements by way of temperature sensors associated with each electrode element, and dependent upon the sensed temperatures, the control device may reselect and implement another alternative firing configuration(s) which uses one or more differing electrode elements to allow the overheated electrode element(s) to cool.

The present invention includes Adaptive Tumor Treating capabilities, which include a wide range of proactive steps that are taken to modify the therapy program (subarray configuration), while allowing the disk temperatures to stabilize or decrease before they reach unacceptable levels. This can be accomplished through implementing alternative subarray configurations that change one or more of the following parameters in the configuration:

1. Duty cycle: a real-time or predictive heat generation, a duration and timing for energizing element, time/duration element is not energized, number of times an element is energized in a program sequence, applied voltage, field strength generated in the body when activated, etc. of an addressable array element.
2. Voltage assigned to subarray configurations for an addressable group of array elements
3. Control of external devices that can aid in the cooling or temperature stabilization of the element (fan, chill pad, etc.).
4. Recommended actions to take by patient and/or caregiver such as shifting body position in a chair or bed, loosening clothing or outer garments, increasing air conditioning of the surroundings, adjusting or turning a fan on, etc. See next invention below.

Furthermore, also in addition to the method 600, as discussed above, the Lifebridge 10000 System may have enhanced patient and/or caregiver recommended actions and positive progress notification for LifeBridge 10000 ATTF system. For out of tolerance conditions (for example over temperature, under temperature, voltage or communications out of tolerances with array elements, etc.) that could potentially be improved or resolved by actions that can be taken by the patient and/or caregivers, enhanced notifications with recommended actions and progress towards improving or resolving the out of tolerance condition are presented. These actions could include shifting position in a chair or bed, loosening or removing clothing items, reseating a loose connection, turning on a fan or other cooling device, facing the array elements in out of tolerance condition more towards a cooling device, checking that an insulated array is properly adhered to the skin, etc.

The system will inform the patient and/or caregivers of the recommended actions via display, tone, voice commands directly from the system and/or via computer or mobile device notification via text, voice, email or computer or mobile application as selected by the patient and/or caregivers.

The system will monitor the out of tolerance condition and provide feedback indicating that the action taken is improving or has resolved the out of tolerance condition on a regular basis (0.5 to 10-minute intervals depending on severity of out of tolerance condition, type of out of tolerance condition, recommended action, etc.) until the condition is resolved, or a preset limit on the number of notifications is reached.

The system will inform the patient and/or caregivers of the effect (improvement, no change or worsening of the out of tolerance conditions) via similar display, tone, voice commands directly from the system and/or via computer or mobile device notification via text, voice, email or computer or mobile application as selected by the patient and/or caregivers. These notification settings can be altered or silenced or stopped based on time of day (i.e. a silent or do not disturb setting). The patient and/or caregiver can stop these notifications via a button or switch on the system, or via command on a website, text or computer or mobile application.

According to another aspect of the present invention, the system, for example the Lifebridge 10000 system, may also perform the following procedure:

1. Are there recommended actions the patient and/or caregiver can take to help mitigate and/or correct the out of tolerance condition?
2. Yes
    a. Energize indicator/display, tone or voice prompt and/or send notification via electronic means to computer or mobile devices stored in system memory
    b. Monitor out of tolerance condition and report improvement, no change or worsening of condition as above
    c. Repeat appropriate notifications until set number, duration of notification time limit, do not disturb period starts, or stop command is received by the system or computer or mobile communications from caregiver or patient
    d. Record time and time of notifications sent, as well as any interactions initiate by patient and/or care givers
3. No:
    a. Follow notification process for that out of tolerance condition.

Figure 7:
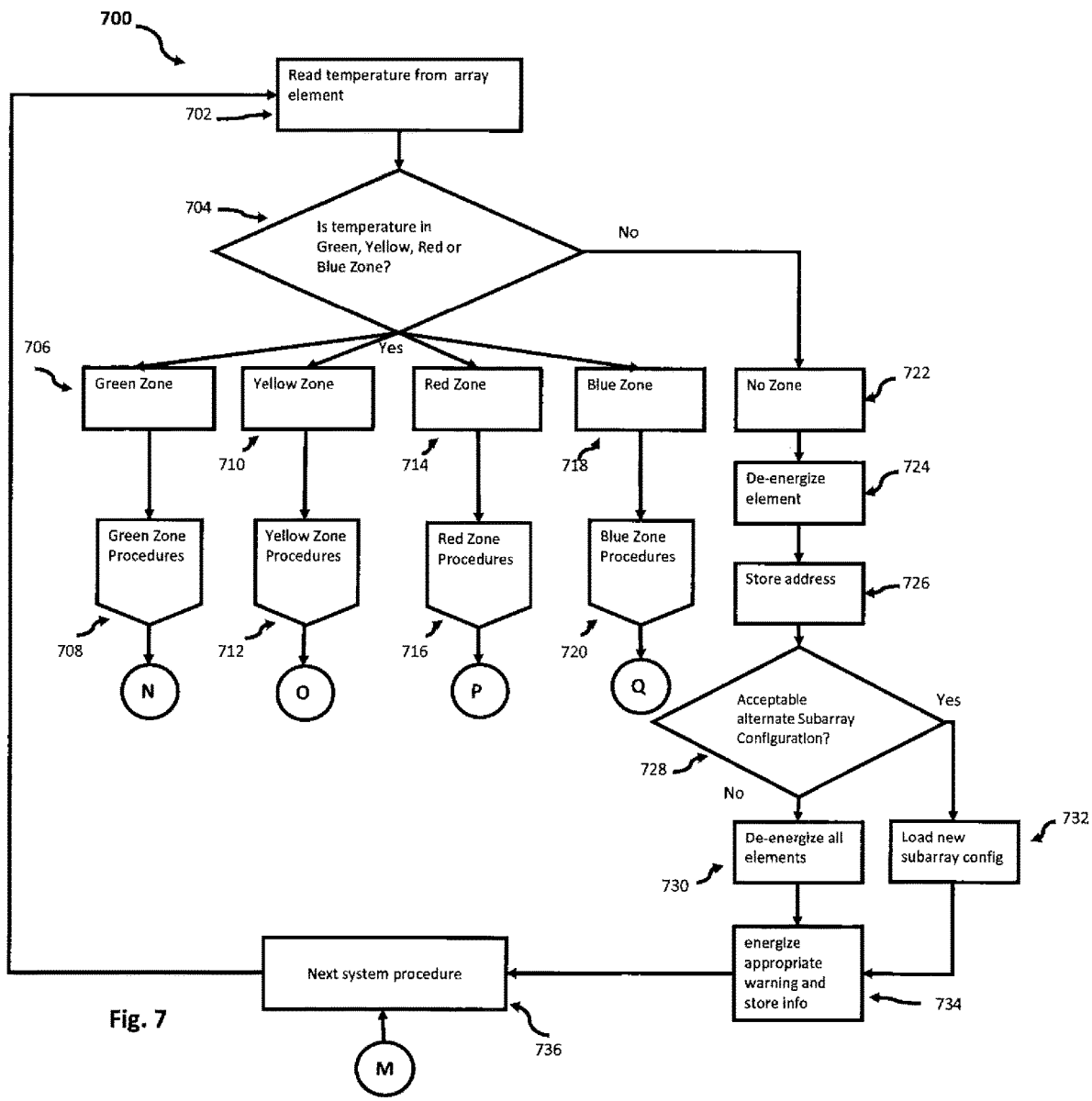
FIG. 7 illustrates a flowchart of a method for an adaptive tumor treating field procedure of the system.

According to another aspect of the present invention, the system, for example the Lifebridge 10000 system, may also perform the following method 700 (FIG. 7). The method 700 may be considered an Adaptive Tumor Treating Field procedure, which is controlled by array element temperature measurements. The method 700 may include: measure array element temperature and report value to System Controller (at block 702). Thereafter, the method 700 may determine if temperature is in Green, Yellow, Red, Blue, or No Zone (at block 704). If the temperature value is in Green Zone (at block 706), the Green Zone system temperature process will be followed (at block 708). If the temperature value is in Yellow Zone (at block 710), the follow Yellow Zone system temperature process will be followed (at block 712). If the temperature value is in Red Zone (at block 714), the Red Zone system temperature process will be followed (at block 716). If the temperature value is in Blue Zone (at block 718), the follow Blue Zone system temperature process will be followed (at block 720). If the measured temperature value is in the No Zone, which means that the temperature is not in the Green, Yellow, Red or Blue Zone (as illustrated in FIG. 7, decision block 704) (at block 722), the method 700 may de-energize the array element (at block 724). Then, the method 700 may store element address with temperature sensor fault for reporting to local or computer or mobile (at block 726). The method will then determine if an alternate acceptable subarray configuration is available (at block 728). If yes, the method 700 may load the new subarray configuration to effected array elements (at block 732). Then, the appropriate warning indicator, tone or both, will be energized (at block 734). If no, the method 700 may de-energize all array elements (at block 730). Thereafter, a warning indicator, tone or both, to reflect appropriate warning, issue warning through text, voice, email, computer or mobile application or other electronic means as appropriate may be energized (at block 734). Then, the method 700 may go to the next system procedure (at block 736).

Figure 8:
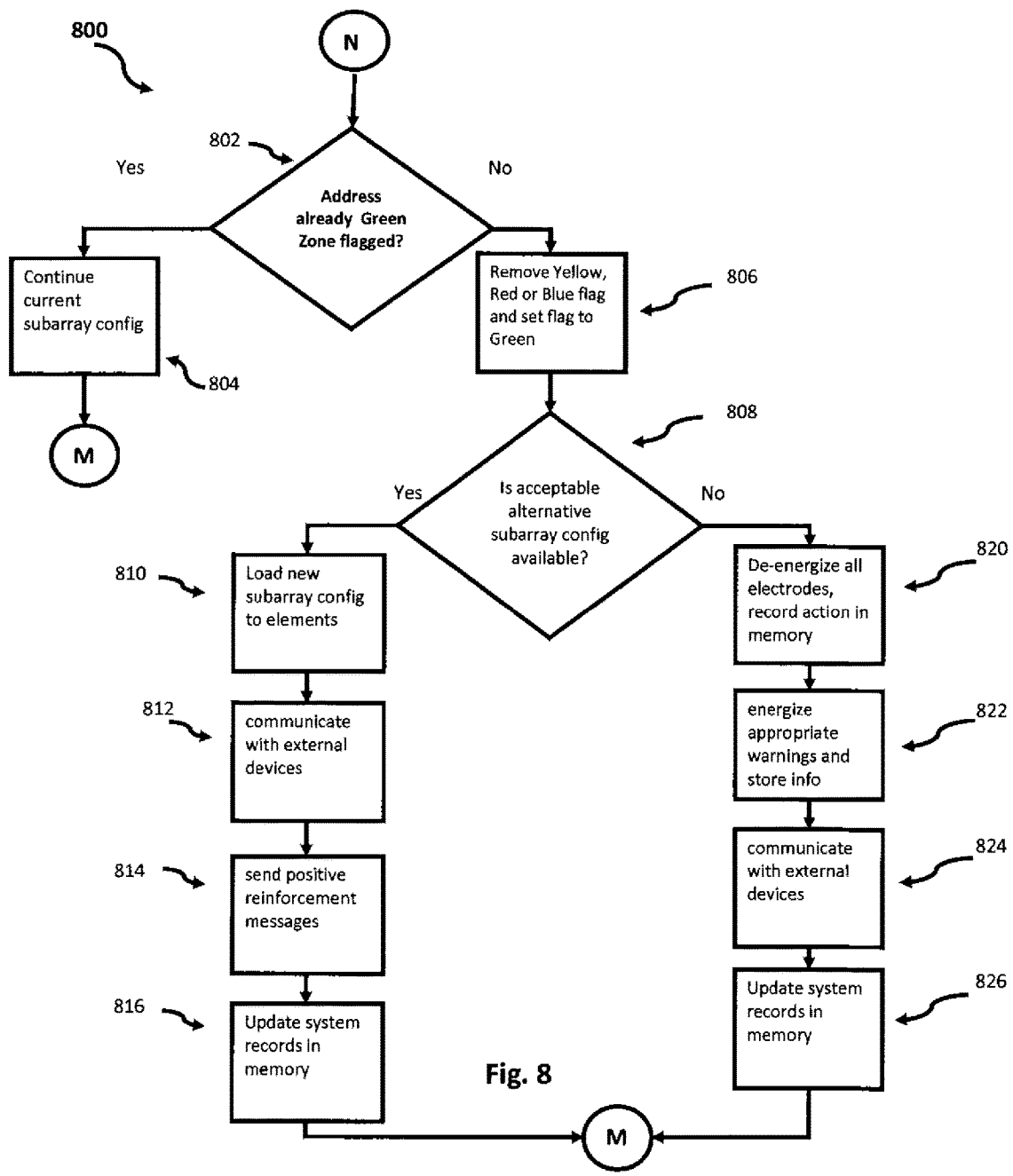
FIG. 8 illustrates a flowchart of a method for a green zone temperature measurement procedure of the system.

The method 800 describes the Green Zone temperature measurement procedure (FIG. 8). The method 800 may have the SC check the memory for the array element address to determine if the address has been stored in the memory with Green, yellow, red or blue temperature flag (at block 802). Green Zone flag: if yes, continue with existing subarray configuration (at block 804); or if no, remove array elopement yellow, red or blue zone flag and record element address with Green Zone flag along with time stamp (at block 806). Thereafter, the method 800 may determine if an alternate acceptable subarray configuration available (at block 808). If yes, a new subarray configuration to effected array elements may be loaded (at block 810). If a device such as a fan, chill pad, cooling garment or other similar device is connected to wired or wireless), so as to be able to be triggered/controlled to change state by Lifebridge 10000 system, the system will switch or communicate with the device or devices to take appropriate action (at block 812). The patient and/or caregiver may be instructed on actions they can take to reduce the temperature of affected array elements as indicated in training, by the warning indicator, through text, email, computer or mobile application or other electronic means (at block 814). The method 800 may record instructions, warnings and state changes in the memory for reporting (at block 816). If no, the method 800 may de-energize all array elements, record time stamp & action (at block 820). Then the method 800 may energize a warning indicator, tone or both to reflect appropriate warning, issue warning through text, email, computer or mobile application or other electronic means as appropriate (at block 822). If a device such as a fan, chill pad, cooling garment or other similar device is connected to wired or wireless), so as to be able to be triggered/controlled to change state by Lifebridge 10000 SC, the SC communicate with the device or devices to take appropriate action (at block 824). The method may record instructions, warnings and state changes in the memory for reporting (at block 826). Then, the method 800 may go to the next system procedure (at block 736).

Figure 11:
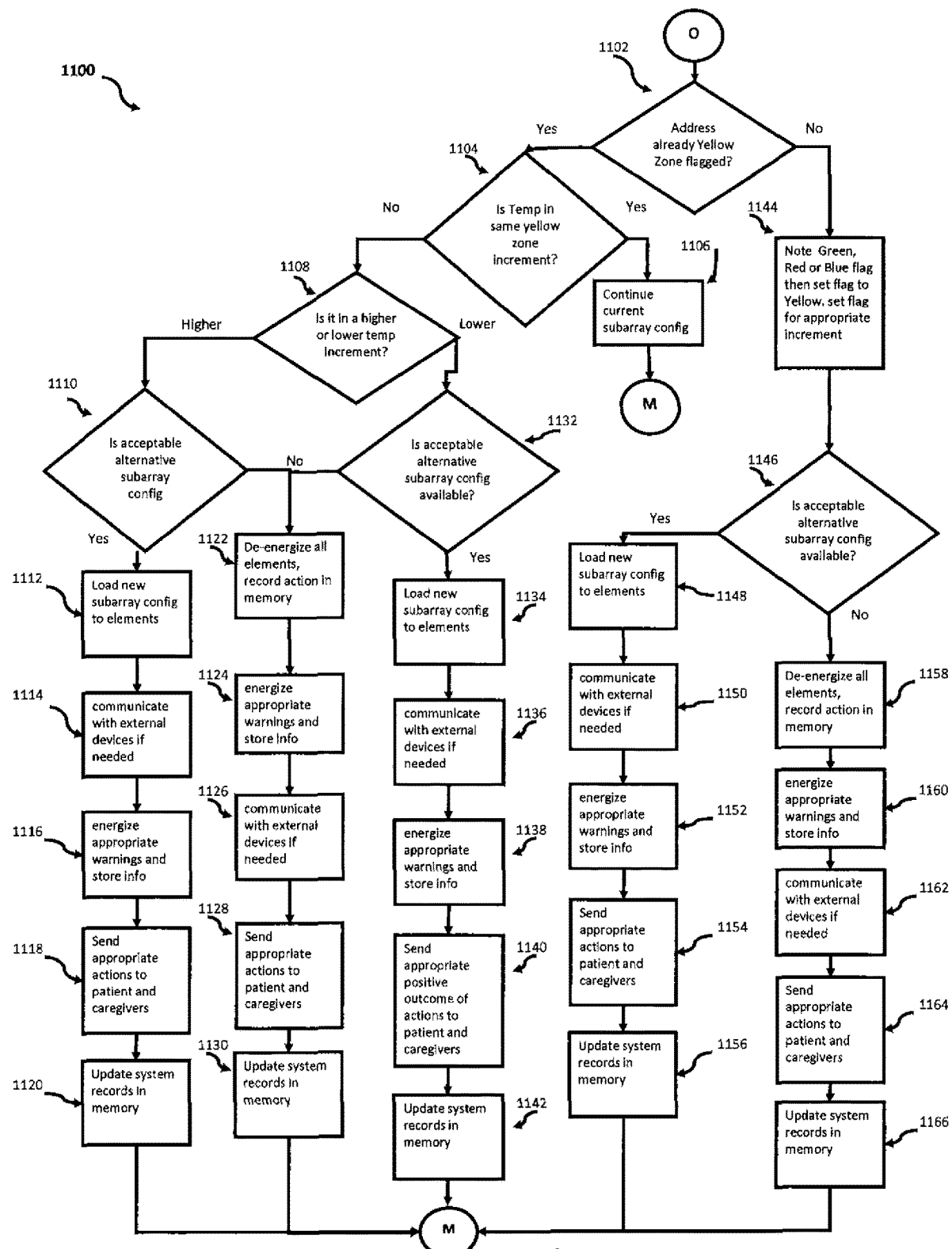
FIG. 11 illustrates a flowchart of a method for a yellow zone temperature measurement procedure of the system.

The method 1100 describes the Yellow Zone temperature measurement procedure (FIG. 11). The method 1100 may have the SC check the memory for an array element address to determine if address has been stored in the memory with yellow temperature flag (at block 1102). If yes, is the temperature in same yellow zone increment as previous measurement (at block 1104)? If yes, the method 1100 will continue with the current subarray configuration (at block 1106). If no, is the temperature measurement in higher or lower increment (at block 1108)? If higher, is the alternate acceptable subarray configuration available (at block 1110)? If yes, the method 1100 will load a new subarray configuration to the array elements (at block 1112). If a device such as a fan, chill pad, cooling garment or other similar device is connected to wired or wireless), so as to be able to be triggered/controlled to change state by Lifebridge 10000 system, the system will switch or communicate with the device or devices to take appropriate action (at block 1114). The method 1100 may then determine if the system will energize warning indicator, tone and/or voice (at block 1116). The patient and/or caregiver may be instructed on actions they can take to reduce the temperature of affected array elements as indicated in training, by the warning indicator, through text, email, computer or mobile application or other electronic means (at block 1118). The instructions and state changes sent to connected devices can be recorded in the memory for reporting (at block 1120). Then, the method 1100 may go to the next system procedure (at block 736). If no, the method 1100 may de-energize all the array elements (at block 1122). Then, the method 1100 may energize a warning indicator, tone or both to reflect appropriate warning (at block 1124). If a device such as a fan, chill pad, cooling garment or other similar device is connected to wired or wireless), so as to be able to be triggered/controlled to change state by Lifebridge 10000 SC, the SC communicate with the device or devices to take appropriate action (at block 1126). The patient and/or caregiver may be instructed on actions they can take to reduce the temperature of affected array elements as indicated in training, by the warning indicator, through text, email, computer or mobile application or other electronic means (at block 1128). The instructions and state changes sent to connected devices can be recorded in the memory for reporting (at block 1130). Then, the method 1100 may go to the next system procedure (at block 736). If the temperature increment is lower, is there an alternate acceptable subarray configuration available (at block 1132)? If yes, load the new subarray configuration to effected array elements (at block 1134). If a device such as a fan, chill pad, cooling garment or other similar device is connected to wired or wireless), so as to be able to be triggered/controlled to change state by Lifebridge 10000 system, the system will switch or communicate with the device or devices to take appropriate action (at block 1136). Then, the method 1100 may determine if the system will de-energize a warning indicator, tone and/or voice notification (at block 1138). The patient and/or caregiver may be instructed on the success of their actions took to reduce the temperature of affected array elements by the warning indicator, through text, email, computer or mobile application or other electronic means (at block 1140). The instructions and state changes can be recorded in the memory for reporting (at block 1142). Then, the method 1100 may go to the next system procedure (at block 736). If there is not an acceptable alternative subarray configuration available, then the method 1100 may de-energize all array elements (at block 1122). Then, a warning indicator, tone or both may be energized to reflect appropriate warning (at block 1124). If a device such as a fan, chill pad, cooling garment or other similar device is connected to wired or wireless), so as to be able to be triggered/controlled to change state by Lifebridge 10000 SC, the SC communicate with the device or devices to take appropriate action (at block 1126). The patient and/or caregiver may be instructed on actions they can take to reduce the temperature of affected array elements as indicated in training, by the warning indicator, through text, email, computer or mobile application or other electronic means (at block 1128). The instructions and state changes sent to the connected devices can be recorded in the memory for reporting (at block 1130). Then, the method 1100 may go to the next system procedure (at block 736). If the address is not already Yellow Zone flagged, the method 1100 may store Green, Red or Blue zone flag from the array element and record element address with new Yellow Zone flag in correct increment (at block 1144). Is alternate acceptable subarray configuration available (at block 1146)? If yes, the new subarray configuration to array element addresses may be loaded (at block 1148). If a device such as a fan, chill pad, cooling garment or other similar device is connected to wired or wireless), so as to be able to be triggered/controlled to change state by Lifebridge 10000 system, the system will switch or communicate with the device or devices to take appropriate action (at block 1150). The patient and/or caregiver may be instructed on actions they can take to reduce the temperature of affected array elements as indicated in training, by the warning indicator, through text, email, computer or mobile application or other electronic means if previous flag was Green (at block 1152). Or, the patient and/or caregiver may be instructed on the success of their actions took to reduce the temperature of affected array elements by the warning indicator, through text, email, computer or mobile application or other electronic means if previous flag was red or Blue (at block 1152). The method 1100 may then energize a warning indicator, tone or both to reflect appropriate warning, issue warning through text, email, computer or mobile application or other electronic means as appropriate (at block 1154). The instructions and state changes can be recorded in the memory for reporting (at block 1156). Then, the method 1100 may go to the next system procedure (at block 736). If no, the method 1100 may de-energize all array elements (at block 1158). The method 1100 may then energize a warning indicator, tone or both to reflect appropriate warning (at block 1160). If a device such as a fan, chill pad, cooling garment or other similar device is connected to wired or wireless), so as to be able to be triggered/controlled to change state by Lifebridge 10000 SC, the SC communicate with the device or devices to take appropriate action (at block 1162). The patient and/or caregiver may be instructed on actions they can take to reduce the temperature of affected array elements as indicated in training, by the warning indicator, through text, email, computer or mobile application or other electronic means if previous flag was Green (at block 1164). Then, the instructions and state changes can be recorded in the memory for reporting (at block 1166). The method 1100 may continue monitoring temperature measurements of all array elements. Then, the method 1100 may go to the next system procedure (at block 736).

Figure 9:
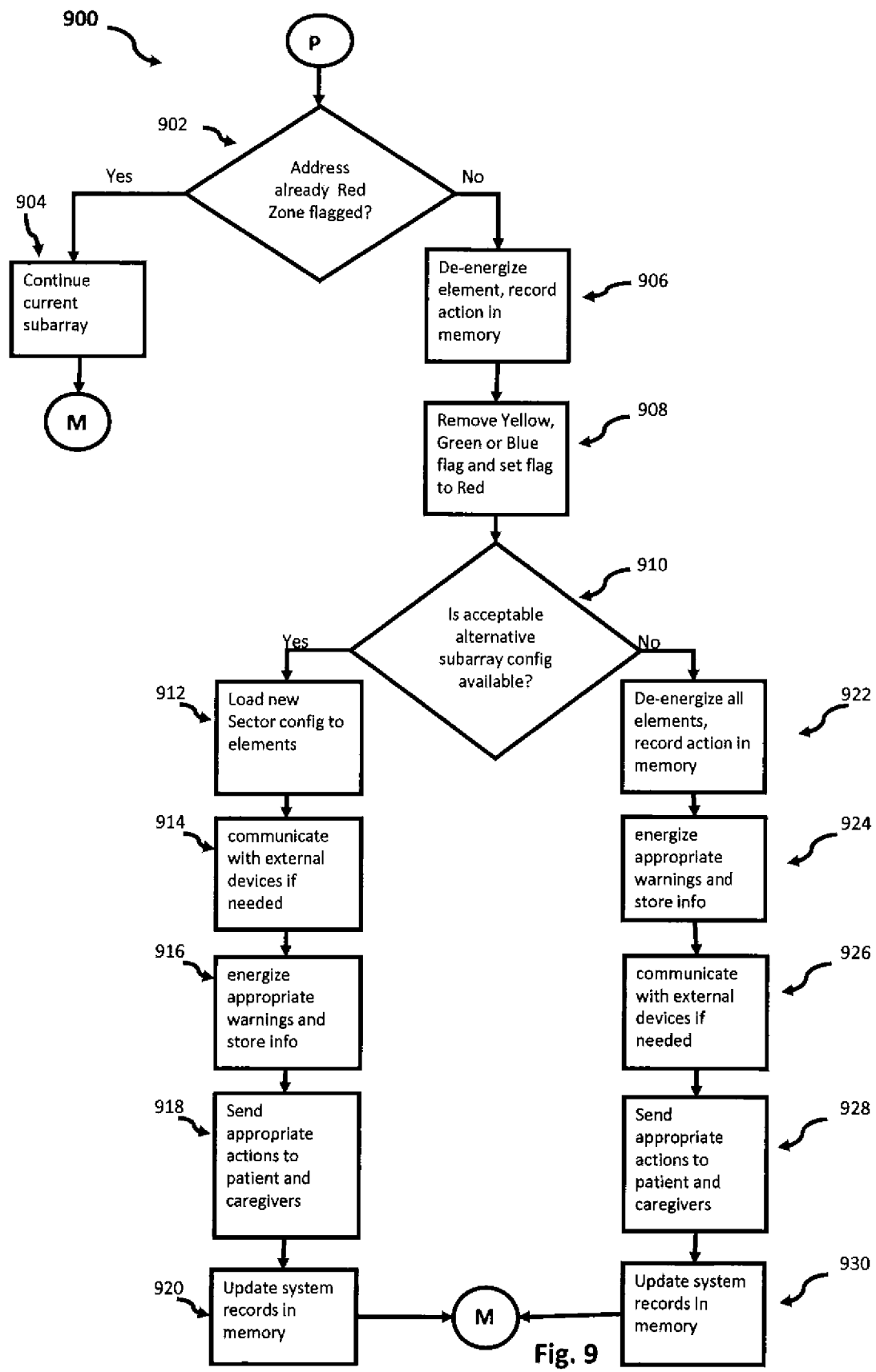
FIG. 9 illustrates a flowchart of a method for a red zone temperature measurement procedure of the system.

The method 900 describes the Red Zone temperature measurement procedure (FIG. 9). The method 900 may have the SC check the memory for an array element address to determine if the address has been stored in the memory with yellow, red or blue temperature flag (at block 902). Red Zone flag: if yes, continue with existing subarray configuration (at block 904); if no de-energize the array element (at block 906). The method 900 may remove Green, Yellow or Blue zone flag from array element address and record element address with Red zone flag (at block 908). Then, the method 900 may determine if an alternate acceptable subarray configuration is available (at block 910). If yes, the method 900 may load a new subarray configuration to effected array elements (at block 912). If a device such as a fan, chill pad, cooling garment or other similar device is connected to wired or wireless), so as to be able to be triggered/controlled to change state by Lifebridge 10000 system, the system will switch or communicate with the device or devices to take appropriate action (at block 914). The method 900 may energize warning indicator, tone or both to reflect appropriate warning, issue warning through text, email, computer or mobile application or other electronic means as appropriate (at block 916). The patient and/or caregiver may be instructed on actions they can take to reduce the temperature of affected array elements as indicated in training, by the warning indicator, through text, email, computer or mobile application or other electronic means (at block 918). The instructions, warnings and state changes can be recorded in the memory for reporting (at block 920). If no, the method 900 may de-energize all array elements (at block 922). The method 900 may energize a warning indicator, tone or both to reflect appropriate warning (at block 924). If a device such as a fan, chill pad, cooling garment or other similar device is connected to wired or wireless), so as to be able to be triggered/controlled to change state by Lifebridge 10000 SC, the SC communicate with the device or devices to take appropriate action (at block 926). The patient and/or caregiver may be instructed on actions they can take to reduce the temperature of affected array elements as indicated in training, by the warning indicator, through text, email, computer or mobile application or other electronic means if previous flag was Green or Yellow Zone (at block 928). The instructions, warnings and state changes can be recorded in the memory for reporting (at block 930). The method 900 may then go to the next system procedure (at block 736).

According to another aspect of the present invention, the system may operate as follows under the Blue Zone. An array element that is failing to efficiently or completely couple the electric field that is being generated typically operates at a lower temperature (operate in the blue temperature zone) than the array elements that are efficiently coupling with the electric field provided those array elements are part of the same subarray firing. Conditions that could affect array element coupling include, poor adhesion to the surface of the skin, or due to an electrical breach in the insulation of the array element or wiring that allows current to flow to the skin, and other similar faulty conditions in the array element.

By comparing the temperature of an array element to the array elements surrounding it (that are included in the same subarray firing), a low temperature condition can be detected, and appropriate action taken.

The system will store a database containing the address of every insulated array element on the patient as well as a list of neighboring subarray elements). The temperature of each individual array element will be compared to other array elements in the same subarray. The suitable neighbor element comparison list can contain from 1 to entire subarray of elements with the same voltage polarity. The number and location of the appropriate neighbors for comparison will vary based on the location, current temperature state and active or deactivated state assignment within the active subarray. This process may be used to track and compare other variables such as voltage, element switch state, etc.).

The system will compare the subarray element to the average and median temperature calculated for the set of neighbor subarray elements identified in the neighbor database.

If an array element's temperature is lower than its neighbor list calculation by 0.5 to 10 degrees (value will depend on primary array element location, system subarray configuration factors (duty cycles, operating voltages, number of active secondary array elements, etc.). then that array element will be removed from all active subarray configurations, flagged with a Blue Zone temperature indicator in the system memory and the SC will determine if an alternative subarray configuration is acceptable or if the system will enter into a safe mode.

Figure 10:
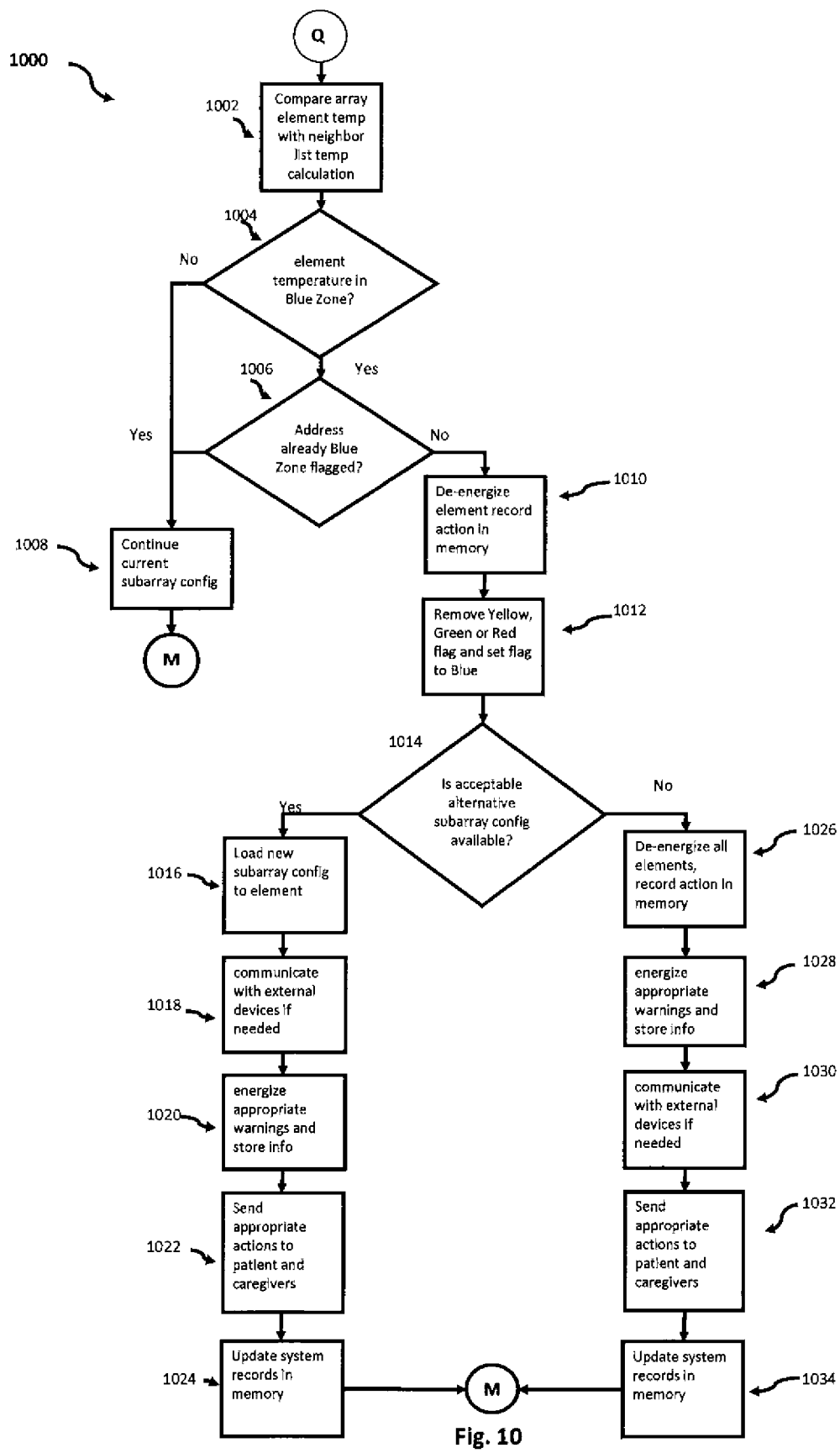
FIG. 10 illustrates a flowchart of a method for a blue zone temperature measurement procedure of the system.

The method 1000 describes the Blue Zone temperature test and procedure (FIG. 10). The method 1000 can create Blue Zone read array element temperatures. The method 1000 may measure and report array element temperature to the SC, and calculate and store average and median neighbor list array element temperatures (at block 1002). The method 1000 can include scaling factors as appropriate in the comparison algorithm (adaptive optimization). Scaling factors are derived from the duty cycle, subarray configuration parameters, element location within the physical arrays, location of the primary array on the body, etc. The method 1000 may include a step of determining whether an array element is in the Blue Zone (at block 1004)? If no, the method 1000 may continue with the current subarray configuration (at block 1008). If yes, does the address have a Blue Zone flag (at block 1006)? If yes, the method 1000 may continue with the existing subarray configuration (at block 1008). Then, the method 1000 may go to the next system procedure (at block 736). If no, the method 1000 may de-energize the array element (at block 1010). Then, the method 1000 may remove the Green, Yellow or Red zone flag from array element address and record element address with Blue Zone flag (at block 1012). Is the alternate acceptable subarray configuration available (at block 1014)? If yes, the new configuration to the effected array elements may be loaded (at block 1016). If a device such as a fan, chill pad, cooling garment or other similar device is connected to wired or wireless), so as to be able to be triggered/controlled to change state by Lifebridge 10000 system, the system will switch or communicate with the device or devices to take appropriate action. The method 1000 can record the instructions and state changes sent to the connected devices (at block 1018). The method 1000 may energize a warning indicator, tone and/or voice to reflect appropriate warning (at block 1020). The patient and/or caregiver may be instructed on actions they can take to reattach or isolate affected array element as indicated in training, by the warning indicator, through text, email, computer or mobile application or other electronic means (at block 1022). The method 1000 may record the instructions, warnings and state changes in the memory for reporting (at block 1024). The method 1000 may then go to the next system procedure (at block 736). If an alternate acceptable subarray is not available, the method 1000 may de-energize all array elements and record actions in the memory (at block 1026). The method 1000 may energize a warning indicator, tone or both to reflect appropriate warning (at block 1028). If a device such as a fan, chill pad, cooling garment or other similar device is connected to wired or wireless), so as to be able to be triggered/controlled to change state by Lifebridge 10000 system, the system will switch or communicate with the device or devices to take appropriate action (at block 1030). The patient and/or caregiver may be instructed on actions they can take to reattach, or isolate affected array element as indicated in training, by the warning indicator, through text, voice, email, computer or mobile application or other electronic means (at block 1032). The instructions, warnings and state changes can be recorded in the memory for reporting (at block 1034). The method 1000 may then go to the next system procedure (at block 736).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and is claimed in the claims.

What is claimed is:

1. A method of delivering tumor-treating electric fields to a body of a patient, comprising:
    receiving a scan of the body of the patient;
    identifying at least two tumor-filled areas on the scan, each tumor-filled area having at least one tumor therein;
    determining a spatial relationship between the at least two tumor-filled areas;
    arranging an array of insulated electrode elements on the body of the patient, the array of insulated electrode elements being coupled to an electric field generator, a control device being configured to send a signal to the electric field generator causing the electric field generator to deliver tumor-treating electric fields to the insulated electrode elements;
    determining at least two subarray firing configurations for the array of insulated electrode elements for targeting the at least two tumor-filled areas, the at least two subarray firing configurations depending at least in part upon the spatial relationship between the at least two tumor-filled areas; and
    delivering the tumor-treating fields to the at least two tumor-filled areas of the patient using the at least two subarray firing configurations.

2. The method of claim 1, further including assigning a respective group of insulated electrode elements of the array of insulated electrode elements to each subarray firing configuration.

3. The method of claim 2, wherein the respective groups of insulated electrode elements share some common insulated electrode elements of the array of insulated electrode elements.

4. The method of claim 2, wherein the respective groups of insulated electrode elements do not share any common insulated electrode elements of the array of insulated electrode elements.

5. The method of claim 1, wherein each subarray firing configuration of the array of insulated electrode elements is implemented simultaneously such that the at least two tumor-filled areas are simultaneously treated.

6. The method of claim 1, wherein each subarray firing configuration of the array of insulated electrode elements is implemented sequentially such that the at least two tumor-filled areas are sequentially treated.

7. The method of claim 1, further including determining the at least two subarray firing configurations depending upon one or more of a triage strategy, a duty cycle of each insulated electrode element, a sensed temperature of each insulated electrode element, a peak power consumption of the array of insulated electrode elements, and a total power consumption of the array of insulated electrode elements.

8. The method of claim 1, further including conducting an adaptive optimization process by sensing a temperature of each insulated electrode element, determining when the sensed temperature is in one of the following zones: a Green Zone, a Red Zone, a Blue Zone, and a Yellow Zone, and implementing a temperature process which corresponds to the determined zone.

9. The method of claim 1, further comprising the step of:
triaging the tumors in the at least two tumor-filled areas to obtain a triage strategy.

10. The method of claim 9, wherein triaging includes assigning a priority value to the at least one tumor in each tumor-filled area.

11. The method of claim 10, further including optimizing one or more of a total amount of treatment time dedicated to the at least one tumor in each tumor-filled area, a duration of a field intensity, and a number of angles of electric field delivery depending upon the assigned priority values of the tumors in the at least two tumor-filled areas.

12. The method of claim 10, wherein implementing the at least two subarray firing configurations includes altering the at least two subarray firing configurations depending upon one or more of the priority value of the at least one tumor in each tumor-filled area and a sensed temperature of each insulated electrode element.

13. The method of claim 9, further including re-triaging the tumors in the at least two tumor-filled areas to obtain an updated triage strategy.

14. The method of claim 9, further including determining the at least two subarray firing configurations depending upon one or more of a duty cycle of each insulated electrode element, a sensed temperature of each insulated electrode element, a peak power consumption of the array of insulated electrode elements, and a total power consumption of the array of insulated electrode elements.

15. The method of claim 9, further including conducting an adaptive optimization process by sensing a temperature of each insulated electrode element, determining when the sensed temperature is in one of the following zones: a Green Zone, a Red Zone, a Blue Zone, a Yellow Zone, and implementing a temperature process which corresponds to the determined zone.

16. The method of claim 9, wherein after implementing the at least two subarray firing configurations, the method further includes implementing at least two alternative subarray firing configurations depending upon a preventive therapy regimen.

17. The method of claim 1, further comprising the steps of:
determining if the at least two subarray firing configurations are simultaneously implementable or sequentially implementable; and
simultaneously implementing or sequentially implementing the at least two subarray firing configurations for treating the at least two tumor-filled areas.

18. The method of claim 17, wherein determining if the at least two subarray firing configurations are simultaneously implementable or sequentially implementable depends upon one or more of an interaction of electric fields of the at least two subarray firing configurations, a power availability of the insulated electrode elements, a duty cycle of each insulated electrode element, a sensed temperature of each insulated electrode element, a triage strategy, a peak power consumption of the array of insulated electrode elements, a total power consumption of the array of insulated electrode elements, and a time constraint to maintain optimal therapeutic effect.

19. The method of claim 17, further including triaging the tumors in the at least two tumor-filled areas to obtain a triage strategy, wherein the tumors in the at least two tumor-filled areas are of equal threat, wherein the method further includes conducting an adaptive optimization process by determining if a subarray firing configuration can be terminated so that another subarray firing configuration will optimize treatment of a corresponding tumor-filled area.

20. The method of claim 17, further including triaging the tumors in the at least two tumor-filled areas to obtain a triage strategy, wherein the tumors in the at least two tumor-filled areas are of an unequal threat, wherein the method further includes conducting an adaptive optimization process by determining if a subarray firing configuration can be terminated based upon the priority value of the at least one tumor in a corresponding tumor-filled area.

21. The method of claim 1, further comprising the steps of:
sensing temperatures of the insulated electrode elements of the array of insulated electrode elements; and
implementing at least one alternative subarray firing configuration depending upon the sensed temperatures to treat the at least one tumor-filled area.

22. The method of claim 21, further including identifying at least one overheated insulated electrode element which is used in the at least one initial subarray firing configuration.

23. The method of claim 22, wherein the at least one overheated insulated electrode element is not used in the at least one alternative subarray firing configuration such that the at least one overheated insulated electrode element can cool down.

24. The method of claim 21, further including determining when a sensed temperature of each insulated electrode element is in one of the following zones: a Green Zone, a Red Zone, a Blue Zone, a Yellow Zone, and further implementing a temperature process which corresponds to the determined zone.

* * * * *